United States Patent
Fujiwara et al.

(10) Patent No.: US 8,444,576 B2
(45) Date of Patent: May 21, 2013

(54) BLOOD TEST APPARATUS HAVING BLOOD SENSOR

(75) Inventors: Masaki Fujiwara, Ehime (JP);
Yoshinori Amano, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/237,157

(22) Filed: Sep. 20, 2011

(65) Prior Publication Data

US 2012/0010530 A1    Jan. 12, 2012

Related U.S. Application Data

(62) Division of application No. 12/162,612, filed as application No. PCT/JP2007/051508 on Jan. 30, 2007.

(30) Foreign Application Priority Data

Jan. 31, 2006 (JP) .................. 2006-022039

(51) Int. Cl.
*A61B 5/00* (2006.01)
*A61B 5/151* (2006.01)
*A61B 5/157* (2006.01)

(52) U.S. Cl.
USPC ............. 600/584; 600/583; 606/181

(58) Field of Classification Search
USPC ............ 600/583, 584; 606/181; 204/403.01
See application file for complete search history.

(56) References Cited

U.S. PATENT DOCUMENTS

| | | | |
|---|---|---|---|
| 5,282,950 A | 2/1994 | Dietze et al. | |
| 5,407,554 A | 4/1995 | Saurer | |
| 5,556,533 A | 9/1996 | Nozoe et al. | |
| 5,741,634 A | 4/1998 | Nozoe et al. | |
| 6,004,441 A | 12/1999 | Fujiwara et al. | |
| 6,071,251 A * | 6/2000 | Cunningham et al. | 600/584 |
| 6,206,841 B1 * | 3/2001 | Cunningham et al. | 600/584 |
| 6,309,526 B1 | 10/2001 | Fujiwara et al. | |
| 6,565,738 B1 | 5/2003 | Henning et al. | |
| 6,706,159 B2 | 3/2004 | Moerman et al. | |
| 6,849,052 B2 | 2/2005 | Uchigaki et al. | |
| 6,875,327 B1 | 4/2005 | Miyazaki et al. | |
| 6,911,131 B2 | 6/2005 | Miyazaki et al. | |
| 6,964,871 B2 | 11/2005 | Bell et al. | |
| 6,969,351 B2 * | 11/2005 | Knoll | 600/309 |
| 6,969,450 B2 * | 11/2005 | Taniike et al. | 204/403.01 |
| 7,198,754 B2 * | 4/2007 | Kasahara et al. | 422/82.01 |
| 7,378,007 B2 | 5/2008 | Moerman et al. | |
| 7,556,723 B2 | 7/2009 | Funke et al. | |
| 7,569,126 B2 | 8/2009 | Celentano et al. | |

(Continued)

FOREIGN PATENT DOCUMENTS

| | | |
|---|---|---|
| EP | 1691192 | 8/2006 |
| EP | 1742045 | 1/2007 |

(Continued)

*Primary Examiner* — Sean Dougherty
(74) *Attorney, Agent, or Firm* — Greenblum & Bernstein, P.L.C.

(57) ABSTRACT

A blood test apparatus has a housing, a blood sensor, and a plurality of connectors. The blood sensor has a plurality of connection terminals that are electrically connected with each electrode of the electrode system; and a reference terminal that serves as a reference. The plurality of connectors are configured to connect to the plurality of connection terminals and the reference terminal of the blood sensor attached at a predetermined position in the blood test apparatus, respectively. And also, relations between the reference terminal and each of the plurality of connection terminals are measured to identify the reference terminal automatically.

13 Claims, 34 Drawing Sheets

U.S. PATENT DOCUMENTS

| | | | |
|---|---|---|---|
| 7,645,421 B2 | 1/2010 | Groll | |
| 7,648,617 B2 | 1/2010 | Miyazaki et al. | |
| 7,651,595 B2 * | 1/2010 | Doi et al. | 204/400 |
| 7,691,071 B2 * | 4/2010 | Kojima et al. | 600/583 |
| 7,718,439 B2 | 5/2010 | Groll | |
| 7,785,271 B2 | 8/2010 | Fujiwara et al. | |
| 7,879,211 B2 | 2/2011 | Katsuki et al. | |
| 7,927,290 B2 | 4/2011 | Fujiwara et al. | |
| 7,998,087 B2 | 8/2011 | Amano et al. | |
| 8,211,038 B2 * | 7/2012 | Wang et al. | 600/584 |
| 2002/0130042 A1 | 9/2002 | Moerman et al. | |
| 2002/0179442 A1 | 12/2002 | Miyazaki et al. | |
| 2002/0198444 A1 | 12/2002 | Uchigaki et al. | |
| 2003/0044997 A1 * | 3/2003 | Kasahara et al. | 436/149 |
| 2003/0144608 A1 * | 7/2003 | Kojima et al. | 600/583 |
| 2003/0159945 A1 * | 8/2003 | Miyazaki et al. | 205/777.5 |
| 2004/0060818 A1 * | 4/2004 | Feldman et al. | 204/403.01 |
| 2004/0178066 A1 | 9/2004 | Miyazaki et al. | |
| 2004/0178067 A1 | 9/2004 | Miyazaki et al. | |
| 2004/0215224 A1 * | 10/2004 | Sakata et al. | 606/181 |
| 2005/0011759 A1 | 1/2005 | Moerman et al. | |
| 2005/0123443 A1 | 6/2005 | Fujiwara et al. | |
| 2005/0194251 A1 | 9/2005 | Miyazaki et al. | |
| 2005/0279631 A1 | 12/2005 | Celentano | |
| 2006/0047220 A1 * | 3/2006 | Sakata et al. | 600/583 |
| 2006/0064035 A1 * | 3/2006 | Wang et al. | 600/583 |
| 2006/0243589 A1 * | 11/2006 | Doi et al. | 204/403.01 |
| 2007/0062822 A1 | 3/2007 | Fujiwara et al. | |
| 2007/0131565 A1 | 6/2007 | Fujiwara et al. | |
| 2007/0138026 A1 | 6/2007 | Fujiwara et al. | |
| 2009/0152111 A1 | 6/2009 | Miyazaki et al. | |
| 2009/0318790 A1 | 12/2009 | Fujiwara et al. | |
| 2010/0006432 A1 | 1/2010 | Miyazaki et al. | |
| 2010/0168534 A1 | 7/2010 | Matsumoto et al. | |
| 2010/0168615 A1 | 7/2010 | Amano et al. | |
| 2010/0191148 A1 | 7/2010 | Matsumura et al. | |
| 2010/0243443 A1 | 9/2010 | Miyazaki et al. | |
| 2011/0027816 A1 | 2/2011 | Fujiwara | |

FOREIGN PATENT DOCUMENTS

| | | |
|---|---|---|
| JP | 09-189675 | 7/1997 |
| JP | 2000-000231 | 1/2000 |
| JP | 2000-019147 | 1/2000 |
| JP | 2003-524496 | 8/2003 |
| JP | 2005-110712 | 4/2005 |
| JP | 2006-201154 | 8/2006 |
| WO | 01/41643 | 6/2001 |
| WO | 01/64105 | 9/2001 |
| WO | 2005/103669 | 11/2005 |

* cited by examiner

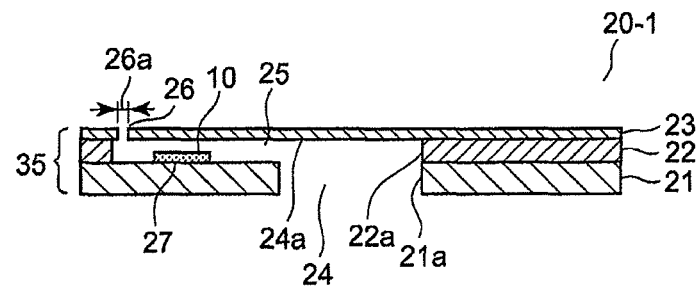
FIG.1A
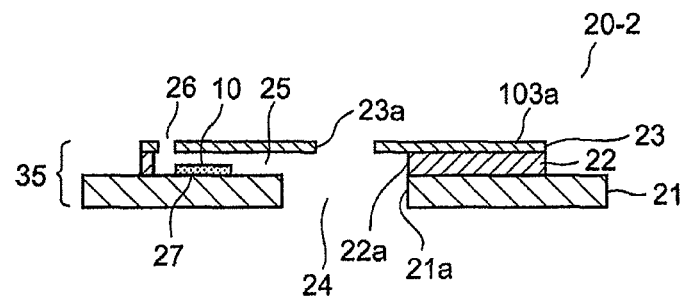
FIG.1B
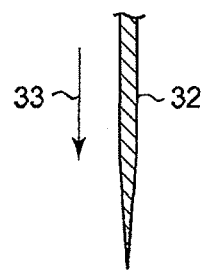
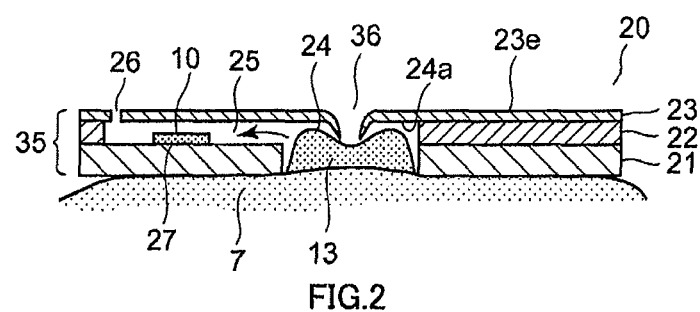
FIG.2

BLOOD TEST APPARATUS HAVING BLOOD SENSOR

CROSS-REFERENCE TO RELATED APPLICATIONS

This application is a division of application Ser. No. 12/162,612, filed Jul. 30, 2008, which was the National Stage of International Application No. PCT/JP2007/051508, filed Jan. 30, 2007.

TECHNICAL FIELD

The present invention relates to a blood sensor and a blood test apparatus with the blood sensor.

BACKGROUND ART

Diabetes patients need to measure the blood sugar level (glucose level) regularly, and inject insulin based on the blood sugar level to maintain a normal blood sugar level. To maintain a normal blood sugar level, diabetes patients need to measure the blood sugar level frequently, sample a small amount of blood from fingertips of the patients using a blood test apparatus, and measure the blood sugar level using this sampled blood and a blood sensor for examining blood.

FIG. 35 is a cross-sectional view showing an example of a conventional blood sensor (see Patent Document 1, for example). Blood sensor 1 shown in FIG. 35 is configured with: substrate 3; spacer 4 provided on the upper surface of substrate 3; and cover 5 provided on the upper surface of spacer 4. Blood storing part 6 is provided so as to penetrate substrate 3 and spacer 4 and blood storing part 6 opens toward the side that abuts on the skin (downward in the figure). One end of blood supply channel 8 is connected to storing part 6 and the other end is connected to air hole 9. Blood detecting section 2 is formed in blood supply channel 8, and reagent 10 is placed on detecting section 2.

FIG. 36A is a perspective plan view of blood sensor 1 seen from above (from the cover 5 side). In the blood sensor shown in FIG. 36A, working electrode 14b and counter electrode 14c function as detection electrodes and form detecting section 2. Further, the blood sensor shown in FIG. 36B is also known (see Patent Document 2). Also in the blood sensor shown in FIG. 36B, working electrode 14b and counter electrode 14c function as detection electrodes and form detecting section 2.

The way to use blood sensor 1 will be described using FIG. 37. FIG. 37 shows a state where needle 11 is pulled up and stays in its original position after blood sampling is finished. First, sensor 1 is brought into contact with skin 7 of the patient. Next, puncturing needle 11 is propelled in the direction of arrow 12. Puncturing needle 11 breaks through cover 5 forming upper side 6a of storing part 6, forms puncturing hole 14 in upper side 6a, and, further, penetrates puncturing hole 14 and scars skin 7. Blood 13 flows out from skin 7 where a scar is made. The outflowing blood 13 fills storing part 6. Blood 13 that fills storing part 6 is led to detecting section 2 through supply channel 8 by capillary action.

Then, blood 13 between working electrode 14b and counter electrode 14c reacts with reagent 10 and produces a current proportional to the blood sugar level. The current produced is led to a measuring circuit in the blood test apparatus via a connector that contacts with connection terminal 15b and a connector that contacts with connection terminal 15c. The measuring circuit measures the current proportional to the blood sugar level and calculates the blood sugar level. The calculated blood sugar level provides basic data and the like showing the amount of insulin to administer to the patient.

To measure the blood sugar level using blood sensor 1 in this way, signals from detection electrode 14b and detection electrode 14c have to be transmitted to the measuring circuit in the blood test apparatus reliably via the connectors.

Patent Document 1: Japanese Patent Application Laid-Open No. 2005-110712
Patent Document 2: Japanese Patent Application Laid-Open No. 2000-000231

DISCLOSURE OF INVENTION

Problems to be Solved by the Invention

When attached to a blood test apparatus, the conventional blood sensor needs to be adjusted its angle of attachment to contact with the connectors of the blood test apparatus at desired positions. Particularly, in recent years, in addition to a working electrode and a counter electrode, a detecting electrode and an Hct electrode (described later) are also going into use as electrode system of a blood sensor. Therefore, to connect the connectors to the connection terminals of the electrode system adequately, it is necessary to adjust their angle of attachment more precisely. For example, if an approximate round blood sensor is attached to a blood test apparatus casually, it is not clear whether connection terminal contacts with the connector, or it is not possible to specify with which of the connectors each connection terminal contacts, and so blood sugar level measurement is not possible. Therefore, the blood sensor may be attached by adjusting the angle of the blood sensor and adjusting the attachment position to a desired position with eyes, using a mark and the like as a reference. However, this attaching work becomes a burden for the patient. Particularly, this work becomes a great burden for diabetes patients with poor eyesight.

It is therefore an object of the present invention to provide a blood sensor that can be attached to a blood test apparatus in a simple manner.

Means for Solving the Problem

The blood sensor of the present invention is characterized in that the blood sensor has a reference terminal which serves as a reference for identifying each of a plurality of connection terminals. For example, the blood sensor of the present invention has: a reference terminal whose electrical resistance with one of the plurality of connection terminals is adjusted to a predetermined value; or two or more reference terminals electrically connected with each other via a conductor.

Advantageous Effect of the Invention

The blood sensor of the present invention has a reference terminal that serves as a reference for identifying each of a plurality of connection terminals, and specifies the individual connection terminals based on the reference terminal. Therefore, the connection terminals can be identified automatically, and the conventional adjustment of the attachment position with eyes is not necessary for attaching the blood sensor, so that the attaching work becomes extremely simple.

BRIEF DESCRIPTION OF DRAWINGS

FIG. 1A is a cross-sectional view of a blood sensor not having a hole in a cover for a puncturing needle to pass through;

FIG. 1B is a cross-sectional view of a blood sensor with a hole in a cover for a puncturing needle to pass through;

FIG. 2 is a cross-sectional view showing a state where blood is brought in the blood sensor;

On the other hand.

BEST MODE FOR CARRYING OUT THE INVENTION

The Blood Sensor

Figure 3:
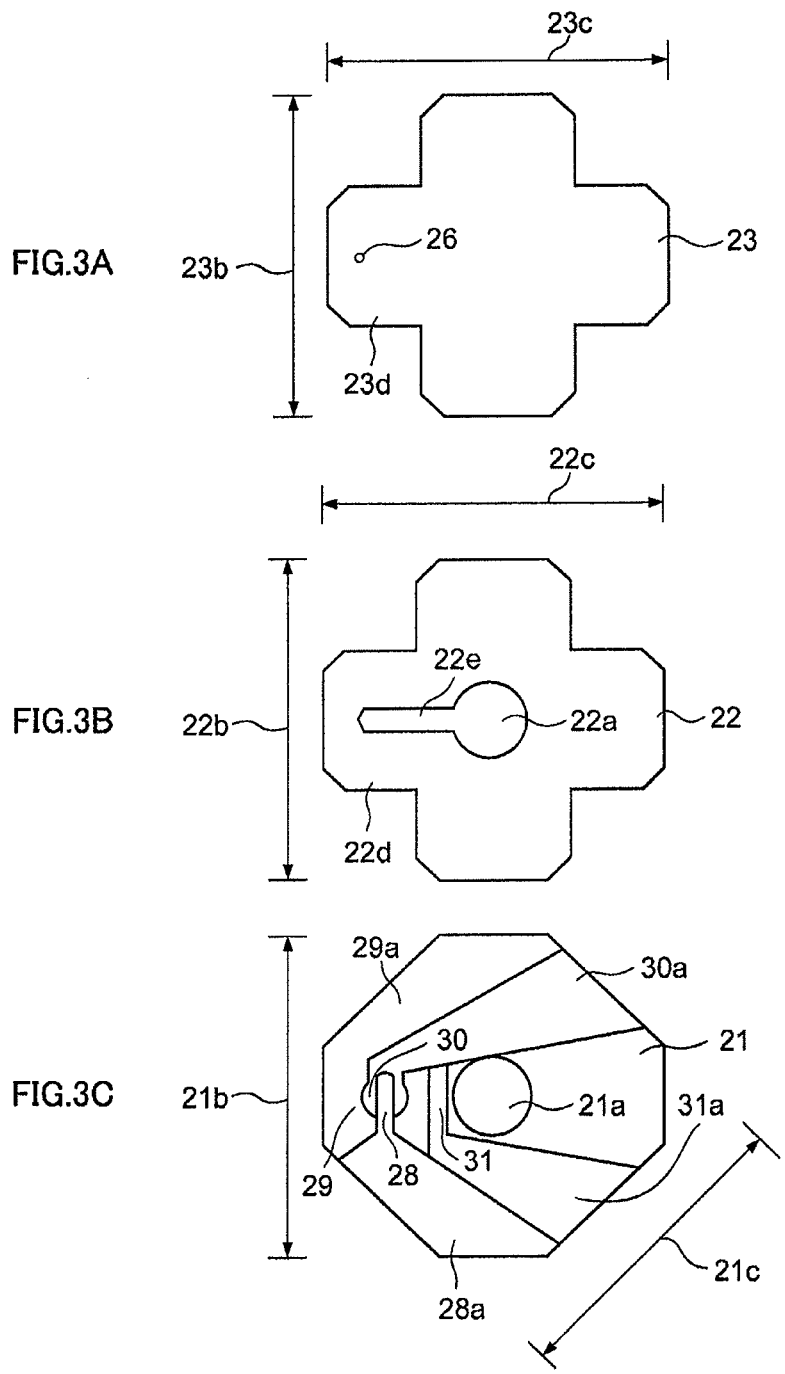
FIG. 3A is a plan view of the cover.
FIG. 3B is a plan view of the spacer.
FIG. 3C is a plan view of the substrate.

The blood sensor of the present invention is a component that is attached to a blood test apparatus and that can be removed or changed. As described later, the blood test apparatus has a plurality of connectors that connect with the blood sensor which is attached at a predetermined position.

FIG. 1A and FIG. 1B are cross-sectional views of blood sensor 20 which is an example of the blood sensor. Blood sensor 20 is formed with base plate 35. Base plate 35 has substrate 21, spacer 22 pasted on the upper surface of substrate 21, and cover 23 pasted on the upper surface of spacer 22.

Blood storing part 24 is provided in base plate 35 of blood sensor 20-1 shown in FIG. 1A and opens toward the side that will be placed on the skin (downward in the figure). Storing part 24 is formed with hole 21$a$ provided in substrate 21 and hole 22$a$ provided in spacer 22. Blood storing part 24 is preferably provided in approximately the center of base plate 35.

One end of supply channel 25 is connected to storing part 24. The blood stored in storing part 24 flows into supply channel 25 by capillary action and is led to detecting section 27. The other end of supply channel 25 is connected to air hole 26.

Reagent 10 is preferably placed on detecting section 27. Detecting section 27, which will be described later, is, for example, placed on substrate 21. Reagent 10 is selected as appropriate depending on the type of the blood component to be measured. When the glucose level is measured, reagent 10 is prepared by dropping on detecting section 27 a reagent solution prepared by adding and dissolving PQQ-GDH (0.1 to 5.0 U/sensor), potassium ferricyanide (10 to 200 mM), maltitol (1 to 50 mM) and taurine (20 to 200 mM) to a 0.01 to 2.0 wt % aqueous solution of CMC, and drying the reagent solution.

In the same way as in blood sensor 20-2 shown in FIG. 1B, hole 23$a$ may be provided in cover 23. Puncturing needle 32 (described later) passes through hole 23$a$. If hole 23$a$ is provided in cover 23 in advance, it is not necessary to open a puncturing hole in cover 23 using puncturing needle 32, so that less force is required upon puncturing, and the damage of the needle tip of puncturing needle 32 is minimized.

[The State where Blood is Brought in the Blood Sensor]

FIG. 2 shows a state where blood is brought in blood sensor 20. First, blood sensor 20 is brought into contact with skin 7 of the patient (such as finger skin). A puncturing means provided in the blood test apparatus makes a scar on skin 7. The puncturing means is puncturing needle 32 in FIG. 2, but the puncturing means is not particularly limited to this and may be a laser, for example. Puncturing needle 32 provided in the blood test apparatus is propelled in the direction of the arrow.

Puncturing needle 32 breaks through cover 23 forming upper side 24a of storing part 24 (when there is no hole 23a in cover 23) and forms puncturing hole 36. Further, puncturing needle 32 makes a scar on skin 7. Blood 13 flows out from skin 7 where a scar is made. The outflowing blood 13 fills storing part 24. Blood 13 then flows into supply channel 27 by capillary action and is led to detecting section 27.

[The Relationship Between the Air Hole and the Puncturing Hole of the Blood Sensor]

Diameter 26a of air hole 26 (see FIG. 1A) is preferably 50 to 500 μm (for example, 50 μm) to prevent blood from flowing out more than necessary from air hole 26. Further, the area of air hole 26 in blood sensor 20-1 is preferably smaller than the area of puncturing hole 36 (hole in cover 23, formed by puncturing needle 32; see FIG. 2). By making the area of puncturing hole 36 larger than air hole 26, most of blood 13 over-sampled in storing part 24 flows out from puncturing hole 36. On the other hand, less blood 13 flows out from air hole 26, and so reagent 10 is less likely to be washed away. Therefore, reagent 10 does not move from detecting section 27, and blood 13 is examined correctly in detecting section 27. In the same way, the area of hole 23a provided in cover 23 in blood sensor 20-2 is preferably larger than that of air hole 26.

[The Water-Repellency and the Hydrophobicity]

First, the area of the reverse side of cover 23 (the surface pasted to the spacer) corresponding to "the inner surface of supply channel 25" is preferably subjected to hydrophilicity treatment to make blood 13 smoothly flow into supply channel 25 by capillary action. Further, the area of the reverse side of cover 23 corresponding to "the upper side of storing part 24" is preferably less hydrophilic than the area of the reverse side of cover 23 corresponding to the inner surface of supply channel 25 to make blood 13 more smoothly flow into supply channel 25 at a constant speed. If blood 13 flows into supply channel 25 at a constant speed and reaches detecting section 27, the melting behavior of reagent 10 exhibits no variation, and the components of blood 13 can be measured correctly.

The surface of cover 23 (the reverse side of the surface pasted to the spacer) is preferably subjected to water-repellency treatment to prevent the blood in storing part 24 from flowing out more than necessary from air hole 26 or a hole in cover 23 (for example, puncturing hole 36 by puncturing needle 32 or hole 23a in the cover). Further, the area of the reverse side of cover 23 corresponding to "the upper side of storing part 24" is preferably less water-repellent than the surface of cover 23 to prevent the blood in storing part 24 from flowing out, more effectively. By preventing blood from flowing out, it is possible to reduce the amount of sampled blood and alleviate the load on the patient.

In the surface of substrate 21, which abuts on the skin, at least the periphery of hole 21a is preferably water-repellent, and the whole surface may be water-repellent. The term "water-repellency" preferably refers to a state where the surface free energy is less than 43 mN/m. When the surface of substrate 21, which abuts on the skin is water-repellent, when the skin is punctured with puncturing needle 32 the blood flowing out can be brought to storing part 24 more easily.

The level of the hydrophilicity or water-repellency is adjusted by performing hydrophilicity treatment or water-repellency treatment. To improve the hydropilicity or water-repellency, hydrophilic material or water-repellent material may be mixed with the material of a member forming blood sensor 20 or hydrophilic material or water-repellent material may be applied to the surface of the member. By adjusting the amount of the hydrophilic material or water-repellent material to be mixed or applied, the level of hydrophilicity or water-repellency is also adjusted. Further, by dissolving or removing hydrophilic material from hydrophobic material (plastic, for example, polyethylene terephthalate) with the hydrophilic material applied on the surface, the hydrophilicity can be reduced. Still further, the characteristic of the hydrophilic material can be adjusted by radiating UV to the hydrophilic material.

Blood sensor 20 with its hydrophilicity or water-repellency controlled as described above, is manufactured using, for example, the following method. In advance, water-repellent treatment is applied to the upper surface of cover 23, and hydrophilic treatment is applied to the lower surface of cover 23. Further, in advance, the whole of the reverse side of substrate 21 (reverse surface of the surface pasted to the spacer) or the periphery of hole 21a, may be subjected to hydrophobic treatment. Next, substrate 21, spacer 22 and cover 23 are pasted (spacer 22 is pasted on the surface of cover 23, where hydrophilicity treatment is applied).

[The Relationship Between the Volume of the Storing Part and the Volume of the Supply Channel]

As described above, blood sensor 20 has blood storing part 24 and blood supply channel 25, and the volume of storing part 24 is one to twenty times, preferably four to fifteen times, and, more preferably, five to seven times as much as the volume of supply channel 25. For example, the volume of storing part 24 in blood sensor 20-1 shown in FIG. 1A may be 0.904 μL, and the volume of blood supply channel 25 may be 0.144 μL. In this way, by controlling the volume ratio between storing part 24 and supply channel 25 adequately, the speed of the blood flowing in supply channel 25 can be controlled to be constant, and the flow rate of the blood flowing in supply channel 25 can be controlled adequately, so that blood does not wash away reagent 10 and reacts with reagent 10 sufficiently, which realizes a correct test.

Further, by controlling the volume ratio between storing part 24 and supply channel 25, it is possible to reduce their volumes. Therefore, the amount of the blood sampled for a test can be reduced, and the load on the patient can be also alleviated.

[The Thickness of the Substrate, Spacer and Cover]

The thickness of substrate 21, spacer 22 and cover 23 of blood sensor 20 and their ratio are important for sampling blood. First, to cause capillary action in supply channel 25, the thickness of spacer 22 preferably falls within a range of 0.05 to 0.15 mm (preferably 0.1 mm).

Further, in blood sensor 20, to adjust the volume of storing part 24 and the volume of supply channel 25, it is necessary to adjust the thickness of spacer 22 and the thickness of substrate 21. The thickness of substrate 21 is preferably the same as the thickness of spacer 22 or greater and preferably falls within the range where the thickness of substrate 21:the thickness of spacer 22=1:1 to 5:1 (preferably, 2.5:1). Further, the thickness of cover 23 is preferably less than the thickness of substrate 21 so that the total thickness of blood sensor 20 is thinner. Therefore, the thickness of substrate 21:the thickness of spacer 22:the thickness of cover 23 may be 2.5:1.3:1 as a reference.

[The Plan View that Disassembles the Blood Sensor]

FIG. 3 is a plan view of disassembled blood sensor 20-1. As described above, blood sensor 20-1 has cover 23 shown in FIG. 3A, spacer 22 shown in FIG. 3B and substrate 21 shown in FIG. 3C.

FIG. 3C is a plan view of substrate 21. Although substrate 21 is an octagon, the shape of the substrate is not particularly limited. The material of substrate 21 is preferably resin such as polyethylene terephthalate (PET). The thickness of substrate 21 preferably falls within a range of 0.075 to 0.25 mm (preferably 0.188 mm).

On one surface of substrate 21 (surface that is pasted with spacer 22), electrode system including electrodes 28 to 31 and connection terminals 28a to 31a connected to electrodes 28 to 31 of the electrode system, respectively, are formed in an integrated manner. Electrode system including electrodes 28 to 31 and connection terminals 28a to 31a are formed by forming a conductive layer using the sputtering method or the vapor deposition method, using gold, platinum, palladium as material and applying laser machining to this conductive layer. Hole 21a is provided in approximately the center of substrate 21, and its diameter may be approximately 2.0 mm.

FIG. 3B is a plan view of spacer 22. The thickness of spacer 22 may fall in a range of 0.05 to 0.15 mm (preferably 0.1 mm). Spacer 22 is preferably a polygon such as an approximate cross shape, because connector 47 (not shown) of the blood test apparatus can be arranged in a cross-shaped dent easily. Hole 22a is provided in approximately the center of spacer 22, at the position matching hole 21a provided in substrate 21. The diameter of hole 22a may be made the same (approximately 2.0 mm) as the diameter of hole 21a. Slit 22e is formed in one convex portion of the cross-shaped spacer 22 from hole 22a. The slit 22e matches blood supply channel 25. By setting the width of the groove of slit 22e 0.6 mm and setting the length in the flow channel direction 2.4 mm, the cavity of supply channel 25 may be set approximately 0.144 µL. In this way, test can be performed with a small amount of blood, so that the load on the patient becomes small, and the patient does not feel fear. The material of spacer 22 may be resin such as polyethylene terephthalate (PET).

FIG. 3A is a plan view of cover 23. Cover 23 has an approximate cross shape, air hole 26 is provided in cross-shaped first convex portion 23d so as to match the tip part of supply channel 25. Preferably, the diameter of air hole 26 is approximately 50 µm.

The material of cover 23 is plastic, and preferably polyethylene terephthalate. The thickness of cover 23 may fall in a range of 0.05 to 0.25 mm (preferably 0.075 mm).

[The Arrangement of Electrodes in the Blood Sensor]

As described above, in blood sensor 20, an electrode system including a plurality of electrodes, connection terminals deriving from each electrode of the electrode system and a reference terminal are arranged. Blood sensor 20 has (1) a reference terminal connected with one of the connection terminals at a predetermined resistance value or (2) two or more reference terminals connected with each other at a predetermined resistance value (preferably 0).

Further, an electrode system arranged in the blood sensor includes at least a "working electrode" and a "counter electrode." The "working electrode" refers to an electrode for measuring blood components, and the "counter electrode" refers to a counterpart electrode of the working electrode. Further, the electrode system arranged in the blood sensor preferably includes a detecting electrode. The "detecting electrode" refers to an electrode for detecting whether blood is supplied to the detecting section. Still further, the electrode system may include an Hct electrode, which refers to an electrode for measuring the hematocrit level of blood.

Blood sensor 20 is preferably a round or a polygon, but the shape is not particularly limited. If blood sensor 20 is a quadrangle or a hexagon, it is possible to improve the yield rate in manufacturing. Further, a hexagon allows a large inscribed circle and is therefore more preferable. That is, if the inscribed circle is the same, the area of the hexagon is smaller than the area of the quadrangle, because of that the hexagon is advantageous.

FIG. 4 to FIG. 9 are perspective plan views of blood sensor 20 and show examples of the arrangement of electrodes in above-described blood sensor 20 (1) that has a reference terminal connected with one of the plurality of connection terminals at a predetermined resistance value. On the other hand, FIG. 10 is a perspective plan view showing an example of the arrangement of electrodes in above-described blood sensor 20 (2) that has two or more reference terminals connected with each other at a predetermined resistance value.

Figure 4:
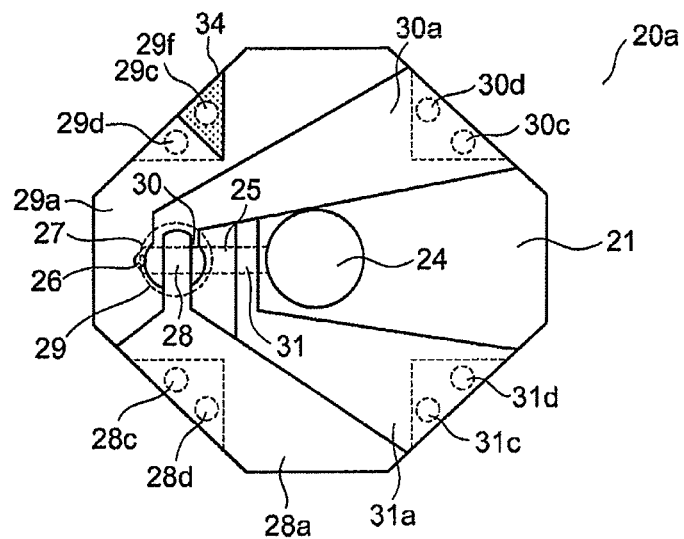
FIG. 4 is a perspective plan view of the blood sensor and shows the arrangement of electrodes, and the like, the blood sensor having a reference terminal insulated from a connection terminal of a detecting electrode, having four pairs of connectors, and having an octagon shape.

Although blood sensor 20a shown in FIG. 4 is an octagon, blood sensor 20a may have other shapes. Electrodes 28 to 31 of the electrode system are formed from storing part 24 toward air hole 26. From storing part 24, electrode 31 as an Hct electrode, electrode 30 as a counter electrode, electrode 28 as a working electrode, (electrode 30 as a counter electrode) and electrode 30 as a detecting electrode, are arranged in that order.

Detecting section 27 is formed on substrate 21, reagent 10 is placed in contact with part of detecting section 27. Reagent 10 is preferably placed in contact with electrode 28 which functions as a working electrode, and electrode 30 which functions as a counter electrode. On the other hand, reagent 10 is preferably not placed in contact with electrode 31 which functions as an Hct electrode.

From electrode system including electrodes 28 to 31, corresponding connection terminals 28a, 29a, 30a and 31a are derived, respectively. Connection terminals 28a to 31a each have contact part that contacts with a connector pair including two connectors. That is, connection terminal 28a has a contact part formed with 28c and 28d, connection terminal 29a has a contact part formed with 29c and 29d, connection terminal 30a has a contact part formed with 30c and 30d, and connection terminal 31a has a contact part formed with 31c and 31d. The contact parts are arranged along the outer periphery of substrate 21.

Only 29c of contact part formed with 29c and 29d is formed on insulating member 34. Therefore, 29c is electrically insulated from 29d, (that is, connection terminals 29a is electrically insulated from 29c), and the resistance between 29c and 29d becomes infinite, while the resistance between 28c and 28d, 30c and 30d, and 31c and 31d becomes zero. To electrically insulate 29c from 29d, 29c may be arranged on insulating member 34 provided on connection terminal 29a, a slit may be provided around 29c, or 29c may be insulated from 29d by cutting out part including contact part 29c from connection terminal 29a.

Further, it is also possible to insulate one of 28c and 28d, 30c and 30d, and 31c and 31d instead of insulating 29c and 29d. That is, one arbitrary connector pair is insulated each other.

29c insulated from 29d (that is, connection terminal 29a) can be used as a reference terminal. When the electrical resistance between the contact parts in pairs is measured, the resistance in one pair is infinite, so that it is possible to specify reference terminal 29c. Based on the specified reference terminal, the connection terminals can be identified, for example, clockwise as connection terminal 29a, connection terminal 30a, connection terminal 31a and connection terminal 28a, and the functions of each electrode of electrode system connected to the connection terminals can be specified.

If blood sensor 20a having a reference terminal is attached to an attaching part (described later) of the blood test apparatus, it is not necessary to consider the relationship between the connectors of the blood test apparatus and the contact parts of the blood sensor, and so it is not necessary to adjust the angle of attachment with eyes, so that attaching a blood sensor becomes simple.

Figure 5:
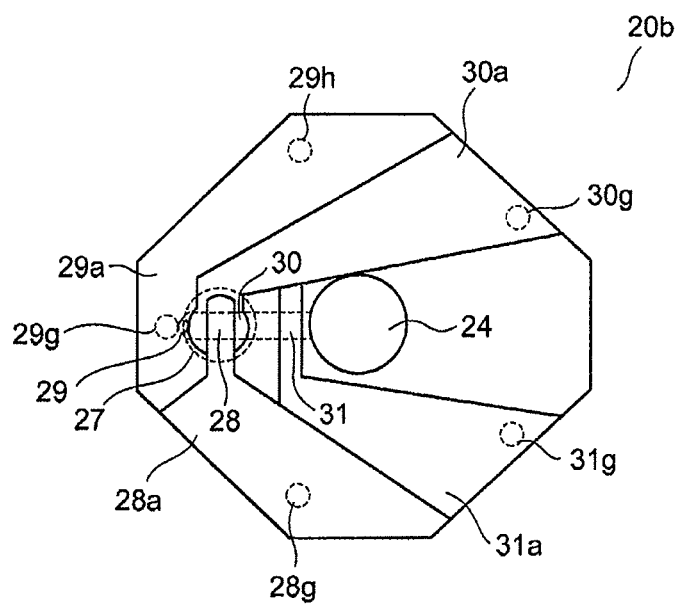
FIG. 5 is a perspective plan view of the blood sensor and shows the arrangement of electrodes, and the like, the blood sensor having a reference terminal connected to a connection terminal of a detecting electrode via a conductor, having five connectors, and having an octagon shape.

Although blood sensor 20b shown in FIG. 5 is an octagon, blood sensor 20b may have other shapes. In the same way as blood sensor 20a, blood sensor 20b has electrode system including electrodes 28 to 31 and connection terminals 28a to 31a deriving from each electrode of the electrode system. Connection terminals 28a to 31a have contact parts 28g to 31g, respectively, and, further, connection terminal 29a has reference contact part 29h in addition to contact part 29g, and 29h serves as a reference terminal. The reference contact part does not have to be provided in connection terminal 29a, but may be provided in any one of connection terminals 28a to 31a. Contact parts 28g to 31g and reference contact part 29h are preferably arranged near the outer periphery at equiangular intervals. For example, a regular pentagon may be formed with parts 28g, 29g, 30g, 31g and 29h. In this way, blood sensor 20b may be made the same as blood sensor 20a except that the mode of the reference contact part is different.

Reference contact part 29h can be specified by measuring the electrical resistance between reference contact part 29h and each of contact parts 28g to 31g. That is, the electrical resistance between one of the contact parts of the connection terminals and reference contact part 29h becomes zero, and so reference contact part 29h can be specified. Using the specified reference contact part as a reference (29h in this example), the connection terminals can be identified clockwise as connection terminals 29a, 30a, 31a and 28a, and the arrangement of the connection terminals can be specified.

Blood sensor 20b has contact parts 28g to 31g and reference contact part 29h, and so the blood test apparatus (described later), to which blood sensor 20b is attached, has five connectors matching the contact parts and the reference contact part. Further, the blood test apparatus has five terminals matching the connectors.

In this way, when blood sensor 20b having a reference terminal is attached to an attaching part (described later) of the blood test apparatus, it is not necessary to consider the relationship between the connectors of the blood test apparatus and the contact parts of the blood sensor, and so it is not necessary to adjust the angle of attachment with eyes, so that attaching a blood sensor becomes simple.

Figure 6:
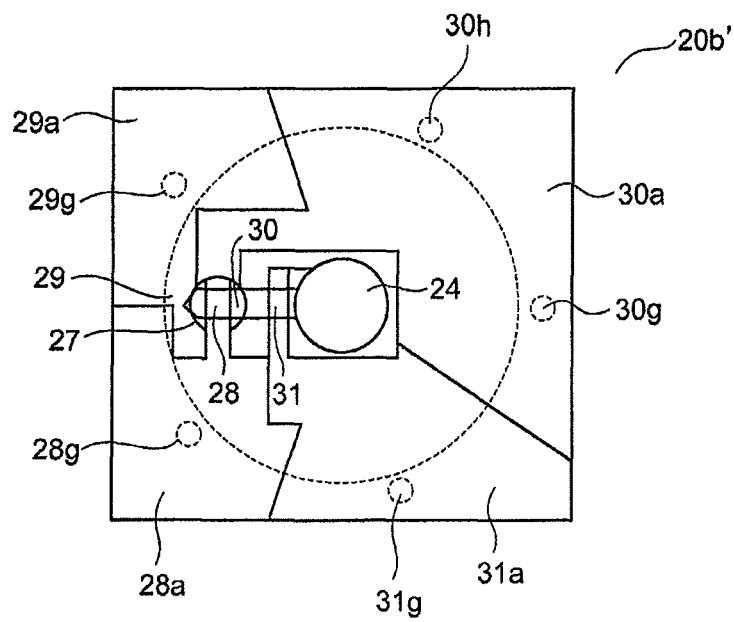
FIG. 6 is a perspective plan view of the blood sensor and shows the arrangement of electrodes, and the like, the blood sensor having a reference terminal connected to a connection terminal of a counter electrode via a conductor, having five connectors, and having a quadrangle shape.

Although blood sensor 20b' shown in FIG. 6 is a quadrangle, blood sensor 20b' may have other shapes. In the same way as blood sensor 20b, blood sensor 20b' has electrode system including electrodes 28 to 31 and connection terminals 28a to 31a deriving from each electrode of the electrode system. Connection terminals 28a to 31a have contact parts 28g to 31g, respectively, and, further, connection terminal 30a corresponding counter electrode 30 has reference contact part 30h in addition to contact part 30g, and 30h serves as a reference terminal. The connection terminals are specified in the same way as in blood sensor 20b.

Figure 7:
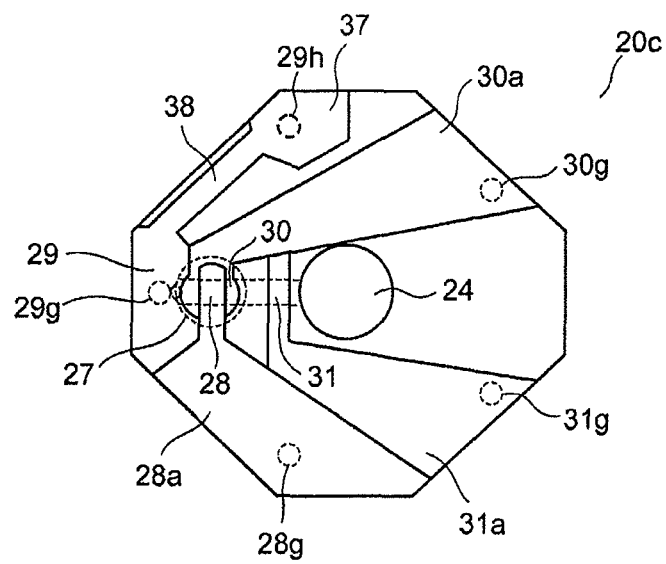
FIG. 7 is a perspective plan view of the blood sensor and shows the arrangement of electrodes, and the like, the blood sensor having a reference terminal connected to a connection terminal of a detecting electrode at a predetermined resistance value, having five connectors, and having an octagon shape.

Although blood sensor 20c shown in FIG. 7 is an octagon, blood sensor 20c may have other shapes. In the same way as blood sensor 20a, blood sensor 20c has electrode system including electrodes 28 to 31 and connection terminals 28a to 31a deriving from each electrode of the electrode system. Connection terminals 28a to 31a have contact parts 28g to 31g, respectively. Further, connection terminal 29a has reference contact part 29h in addition to contact part 29g, and 29h serves as a reference terminal. Reference contact part 29h and contact part 29g are connected at a predetermined resistance value. A reference contact part does not have to be provided in connection terminal 29a but may be provided in any one of connection terminals 28a to 31a. In this way, blood sensor 20c may be made the same as blood sensor 20a except that the mode of the reference contact part is different.

Contact parts 28g to 31g and reference contact part 29h are preferably arranged near the outer periphery at equiangular intervals. For example, a regular pentagon may be formed with contact parts 28g, 29g, 30g, 31g and reference contact part 29h. Therefore, in the same way as the case of blood sensor 20b, the blood test apparatus to which blood sensor 20c is attached, has five connectors and five terminals.

Contact part 29g and reference contact part 29h are connected with pattern (used as an example of predetermined resistance) 38 which is patterned by laser machining in connection terminal 29a. By changing the width of pattern 38, it is possible to adjust the resistance value between contact part 29g and reference contact part 29h to a predetermined value. Therefore, reference contact part 29h can be specified by measuring the electrical resistance between reference contact part 29h and each of contact parts 28g to 31g. That is, the electrical resistance between one of the contact parts of the connection terminals and reference contact part 29h becomes a predetermined value, and so the reference contact part can be specified. Based on the specified reference contact part (29h in this example), the connection terminals can be identified clockwise as connection terminals 29a, 30a, 31a and 28a, and the arrangement of the connection terminals can be specified.

Reference contact part 29h can be also used to determine the type of blood sensor 20c other than used as a reference terminal. Examples of determining the type of the blood sensor include setting the blood test apparatus so that calibration curve 1 is used when the resistance value of pattern 38 is 200 to 1000 ohms, calibration curve 2 is used when the resistance value is 1000 to 2000 ohms, and calibration curve 3 is used when the resistance value is 2000 to 3000 ohms, determining the type of the blood sensor from the resistance value, and automatically selecting the calibration curve to be applied. Further, it is also possible to determine the product specifications of shipped blood sensors, for example, the specification for company A and the specification for company B, depending on the resistance values of pattern 38. Further, by changing an oscillation frequency according to an inductance value adjusted by pattern 38 so that configuring blood sensor 20c has various information, the blood sensor can be determined using the information.

When blood sensor 20c having reference contact part 29h, which serves as a reference terminal, is attached to an attaching part (described later) of the blood test apparatus, it is not necessary to consider the relationship between the connectors of the blood test apparatus and the contact parts of the blood sensor, and so it is not necessary to adjust the angle of attachment with eyes, so that attaching a blood sensor becomes simple.

Figure 8:
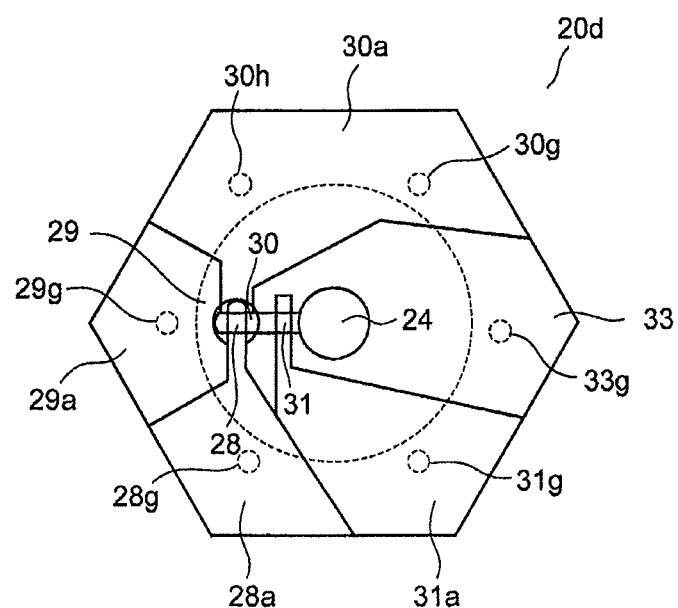
FIG. 8 is a perspective plan view of the blood sensor and shows the arrangement of electrodes, and the like, the blood sensor having a reference terminal connected to a connection terminal of a counter electrode via a conductor and a dummy electrode, having six connectors, and having a hexagon shape.

Although blood sensor 20d shown in FIG. 8 is a hexagon, blood sensor 20d may have other shapes. Blood sensor 20d has electrode system including electrodes 28 to 31 and connection terminals 28a to 31a deriving from each electrode of the electrode system. Connection terminals 28a to 31a have contact parts 28g to 31g, respectively. Further, connection terminal 30a has reference contact part 30h used as a reference terminal in addition to contact part 30g. The reference contact part does not have to be provided in connection terminal 30a but may be provided in any one of connection terminals 28a to 31a.

Further, blood sensor 20d also has dummy electrode 33. The dummy electrode is provided to maintain mechanical balance (balance of the contact positions). Contact part 33g is arranged on dummy electrode 33. Therefore, the blood test apparatus to which blood sensor 20d is attached, has six connectors.

Contact parts 28g to 31g and reference contact part 30h are preferably arranged near the outer periphery of blood sensor 20d at equiangular intervals. For example, a regular hexagon may be formed with parts 28g to 31g, 30h and 33g.

The reference contact part 30h can be specified by measuring the electrical resistance between reference contact part 30h, and each of contact parts 28g to 31g and contact part 33g of dummy electrode 33. That is, the electrical resistance between one of the contact parts and reference contact part 30h becomes zero, and so reference contact part 30h can be specified. Using the specified reference contact part as a reference (30h in this example), the connection terminals can be identified clockwise as connection terminal 30a, dummy electrode 33, connection terminal 31a of an Hct electrode, connection terminal 28a of a working electrode and connection terminal 29a of a detecting electrode, and the arrangement of the connection terminals can be specified.

Figure 9A:
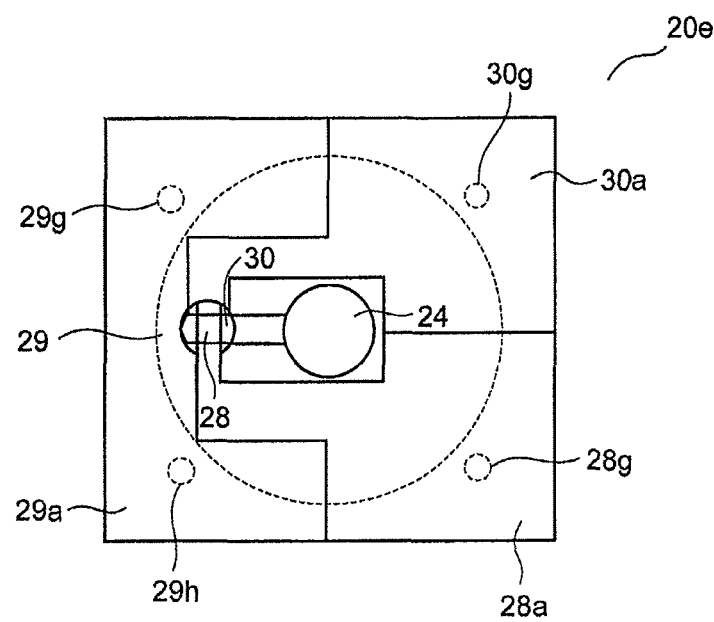
FIG. 9A is a perspective plan view of the blood sensor and shows the arrangement of electrodes, and the like, the blood sensor having a detecting electrode, a working electrode, a counter electrode and a reference terminal, but does not have an Hct electrode, having four connectors, and having a regular square shape.
Figure 9B:
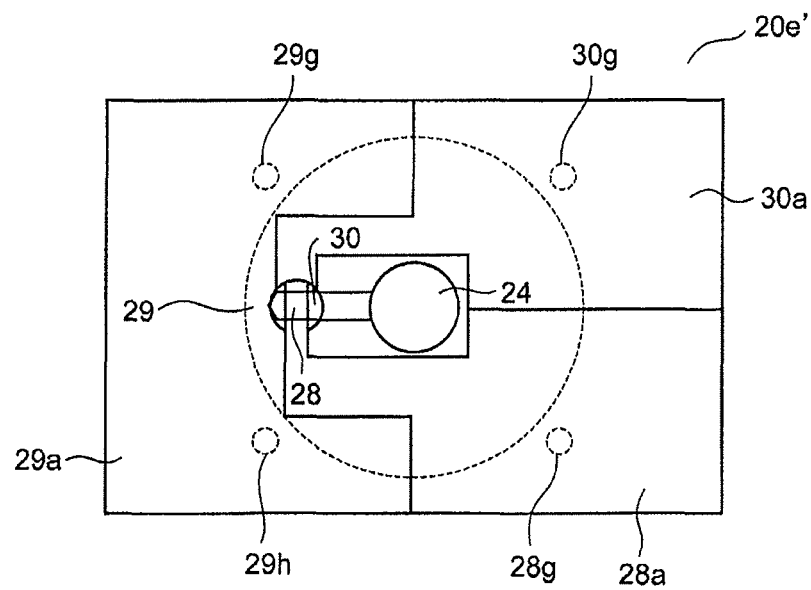
FIG. 9B is a perspective plan view of the blood sensor and shows the arrangement of electrodes, and the like, the blood sensor having a detecting electrode, a working electrode, a counter electrode and a reference terminal, but doe not have an Hct electrode, having four connectors, and having a rectangle shape.
Figure 10:
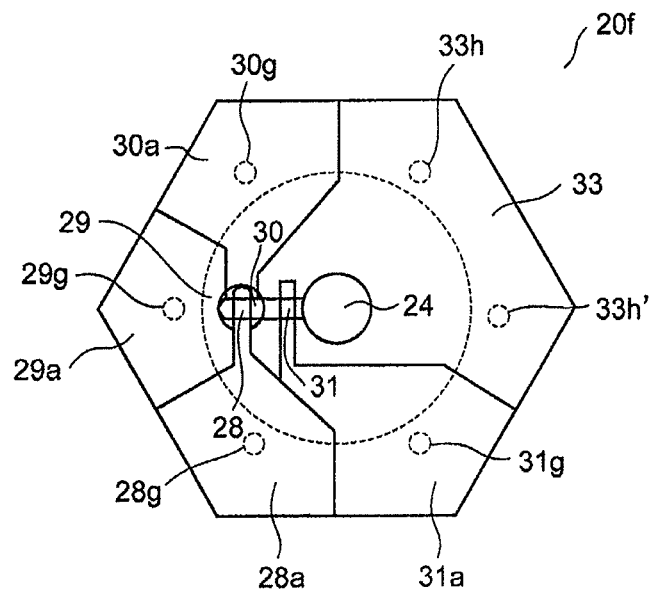
FIG. 10 is a perspective plan view of the blood sensor and shows the arrangement of electrodes, and the like, the blood sensor having two reference terminals and six connectors, and having a hexagon shape.

Although blood sensor 20e shown in FIG. 9A is a regular square and blood sensor 20e' shown in FIG. 9B is a rectangle, blood sensor 20e and blood sensor 20e' may have other shapes. Blood sensors 20e and 20e' have electrode 28 for a working electrode, electrode 29 for a detecting electrode, and electrode 30 for a counter electrode, and are different from above-described blood sensors 20a to 20d in that blood sensors 20e and 20e' do not have electrode 31, which is an Hct electrode.

Further, blood sensors 20e and 20e' have connection terminals 28a to 30a deriving from electrodes 28 to 30, respectively, and contact parts 28g to 30g are arranged in connection terminals 28a to 30a, respectively. Further, connection terminal 29a has reference contact part 29h in addition to contact part 29g, and 29h serves as a reference terminal. Therefore, four connectors are arranged in the blood test apparatus to which blood sensor 20e is attached. Parts 28g to 30g and 29h are preferably arranged near the outer periphery of blood sensor 20e or 20e' at equiangular intervals. For example, a regular square may be formed with contact parts 28g to 30g and reference contact part 29h. The reference contact part does not have to be provided in connection terminal 29a but may be provided in any one of connection terminals 28a to 30a.

The reference contact part 29h can be specified by measuring the electrical resistance between reference contact part 29h and each of contact parts 28g to 30g. That is, the electrical resistance between one of the contact parts and reference contact part 29h becomes substantially zero, and so reference contact part 29h can be specified. Using the specified reference contact part as a reference (29h in this example), the connection terminals can be identified clockwise as connection terminals 29a, 30a and 28a, and the arrangement of the connection terminals can be specified.

Although blood sensor 20f shown in FIG. 10 is a hexagon, blood sensor 20f may have other shapes. Blood sensor 20f has electrode system including electrodes 28 to 31 and connection terminals 28a to 31a deriving from each electrode of the electrode system. Contact parts 28g to 31g are arranged in connection terminals 28a to 31a, respectively. Further, blood sensor 20f has electrode 33, and two reference contact parts 33h and 33h', which serve as reference terminals, are arranged in electrode 33. Contact parts 28g to 31g and reference contact parts 33h and 33h' are preferably arranged near the outer periphery at equiangular intervals. Six connectors are arranged in the blood test apparatus to which blood sensor 20f is attached.

Reference contact parts 33h and 33h', which serve as reference terminals, are connected via a conductor, and so the resistance between 33h and 33h' becomes zero. Therefore, a pair of reference terminals (33h and 33h') between which the resistance becomes zero is specified. Using the specified reference terminal as a reference, the connection terminals can be identified clockwise as connection terminals 31a, 28a, 29a and 30a, and the arrangement of the connection terminals can be specified.

[The Blood Sensor with an Attaching Guide]

Blood sensor 20 preferably has an attaching guide. The attaching guide is a component for attaching blood sensor 20 at a predetermined position of the blood test apparatus. The predetermined position is a position where a plurality of connectors of the blood test apparatus are connected with contact parts of the connection terminals of the blood sensor and a contact part which serves as a reference terminal. Further, at the predetermined position, the plurality of connectors do not contact with the boundaries between the electrodes of the blood sensor.

The connectors of the blood test apparatus preferably contact with the periphery of the axis of the blood sensor attached at the predetermined position. The axis of the blood sensor is near the axis of the rotation of the blood sensor when the blood sensor is inserted to the attaching part of the blood test apparatus. Further, the axis of the blood sensor may be near the center of the part where the blood sensor unit (which is, for example, a blood sensor or a cartridge including a blood sensor) and the attaching part of the blood test apparatus engage with each other. The axis of the blood sensor is usually inside storing part 24 on the surface of the substrate of the blood sensor.

The attaching guide preferably adjusts as appropriate the rotation angle with respect to the axis of attached blood sensor 20 to the blood test apparatus. That is, the attaching guide may be (1) a guide that adjusts the rotation angle with respect to the axis of the blood sensor 20 to angles other than an undesirable angle, that is, the guide prevents blood sensor 20 from being led to certain undesirable positions, or (2) a guide that adjusts the rotation angle with respect to the axis to a predetermined angle, that is, leads blood sensor 20 to a predetermined position selectively.

FIG. 11 to FIG. 15 show examples of combination of blood sensor 20 integrated with holder 80 having attaching guide 81 that prevents a blood sensor from being led to certain undesirable positions and attaching part 90 of the blood test apparatus to which blood sensor 20 is attached. In this case, a "certain undesirable position" refers to a position where the connectors of the blood test apparatus are placed at the boundaries between the electrodes (such as connection terminals and a dummy electrode) formed in blood sensor 20, because, if the connectors of the blood test apparatus contact with the boundaries between the electrodes of blood sensor 20, measurement is not possible.

On the other hand, FIG. 16 and FIG. 17 show examples of combination of blood sensor 20 with holder 80 that leads blood sensor 20 to a predetermined position selectively, and attaching part 90 of the blood test apparatus, to which blood sensor 20 is attached.

Figure 11A:
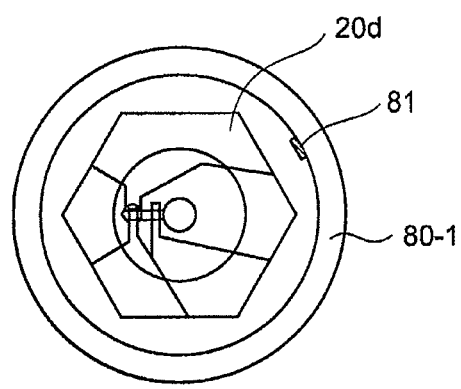
FIG. 11A shows a blood sensor with an attaching guide.

FIG. 11A shows blood sensor 20d with holder 80-1. Blood sensor 20d is the same as the blood sensor shown in FIG. 8, is a hexagon, and has four connection terminals 28a to 31a deriving from the four electrodes of the electrode system and dummy electrode 33. Contact parts 28g to 31g are arranged in connection terminals 28a to 31a, respectively, contact part 33g is arranged in dummy electrode 33, and, further, reference contact part 30h, which serves as a reference terminal, is arranged in connection terminal 30a On the other hand, holder 80-1 is fixed and arranged so as to surround blood sensor 20d and has one attaching guide 81 in its inner periphery.

Figure 11B:
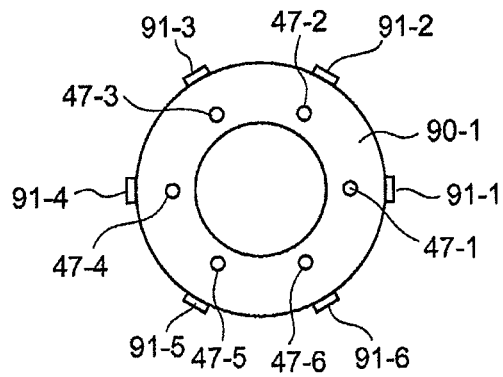
FIG. 11B shows an attaching part of the blood test apparatus to which the blood sensor shown in FIG. 11A is attached.

FIG. 11B shows attaching part 90-1 of the blood test apparatus to which blood sensor 20d with holder 80-1 is attached. Attaching part 90-1 has six connectors 47-1 to 47-6, and attaching part 90-1 has six attaching guides 91-1 to 91-6 on the outer surface. Each of connectors 47 and attaching guides 91 are preferably arranged at equiangular intervals on the circle line.

It is also possible to arrange six attaching guides 81 on the inner surface of holder 80-1 and one attaching guide 91 on the outer surface of attaching part 90-1.

Figure 11C:
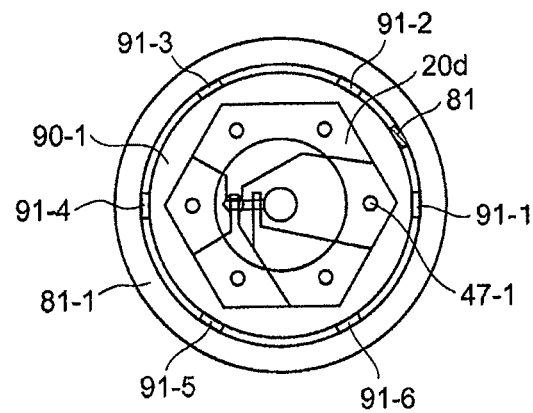
FIG. 11C shows a state where the blood sensor is attached to the attaching part which prevents the blood sensor from being attached at undesirable positions.
Figure 11D:
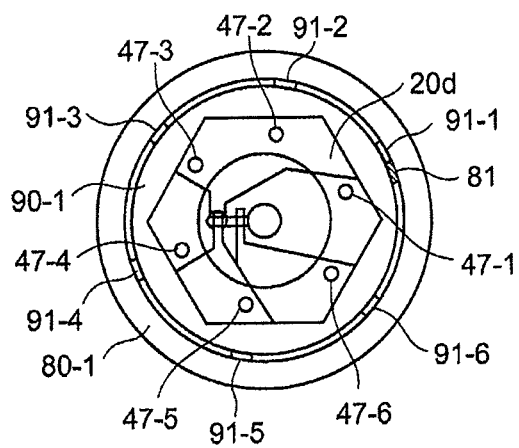
FIG. 11D shows a state where the blood sensor is attached to the attaching part, which prevents the blood sensor from being attached at undesirable positions.

FIG. 11C and FIG. 11D show a state where blood sensor 20d with holder 80-1 is attached to attaching part 90-1 of the blood test apparatus. Four connectors (47-2 or 47-3, 47-4, 47-5 and 47-6 in the figure) out of six connectors of attaching part 90-1 contact with contact parts 28g to 31g of connection terminals 28a to 31a one by one, one connector (47-3 or 47-2 in the figure) contacts with reference contact part 30h provided in connection terminal 30a, and the remaining one connector (47-1 in the figure) contacts with contact part 33g formed in dummy electrode 33. As shown in FIG. 11C and FIG. 11D, attaching guide 81 on the inner surface of holder 80-1 and attaching guides 91 on the outer surface of attaching part 90-1 are defined by each other and prevents connectors 47 of the attaching part from being arranged on the boundaries between the connection terminals of blood sensor 20d.

As described above, it is possible to specify reference terminal 30h and specify the connection terminals based on reference terminal 30h.

Figure 12A:
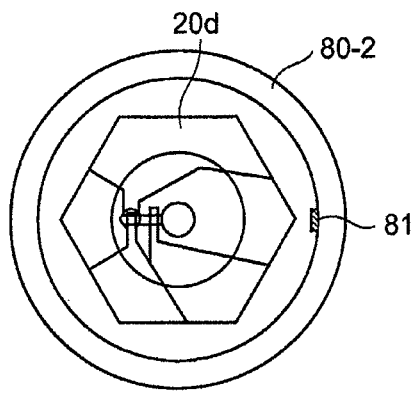
FIG. 12A shows a blood sensor with an attaching guide.
Figure 12B:
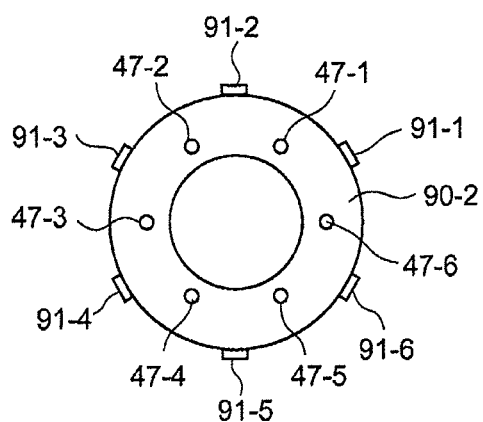
FIG. 12B shows an attaching part of the blood test apparatus to which the blood sensor shown in FIG. 12A is attached.

FIG. 12A shows blood sensor 20d with holder 80-2. Holder 80-2 is the same as holder 80-1 in FIG. 11A in that holder 80-2 is arranged so as to surround blood sensor 20d and has one attaching guide 81 in its inner periphery, but holder 80-2 is different from holder 80-1 in the positional relationship between attaching guide 81 and blood sensor 20d. Further, attaching part 90-2 shown in FIG. 12B is different from attaching part 90-1 shown in FIG. 11B in the positions of attaching guides 91. Each of connectors 47 and attaching guides 91 of attaching part 90-2 are preferably arranged at equiangular intervals on the circle.

Figure 12C:
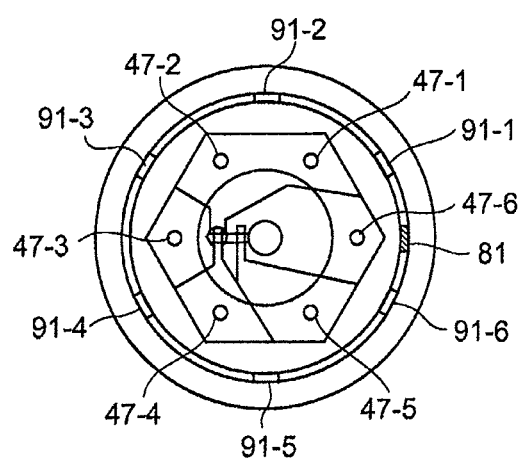
FIG. 12C shows a state where the blood sensor is attached to the attaching part, which prevents the blood sensor from being attached at undesirable positions.
Figure 12D:
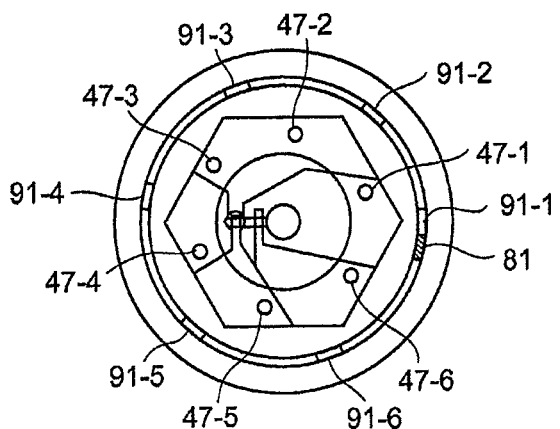
FIG. 12D shows a state where the blood sensor is attached to the attaching part, which prevents the blood sensor from being attached at undesirable positions.

When blood sensor 20d with holder 80-2 is attached to attaching part 90-2 shown in FIG. 12B, as shown in FIG. 12C and FIG. 12D, attaching guide 81 of holder 80-2 and attaching guides 91 of attaching part 90-2 are defined by each other and prevents connectors 47 of attaching part 90-2 from being arranged on the boundaries between the connection terminals of blood sensor 20d.

Figure 13A:
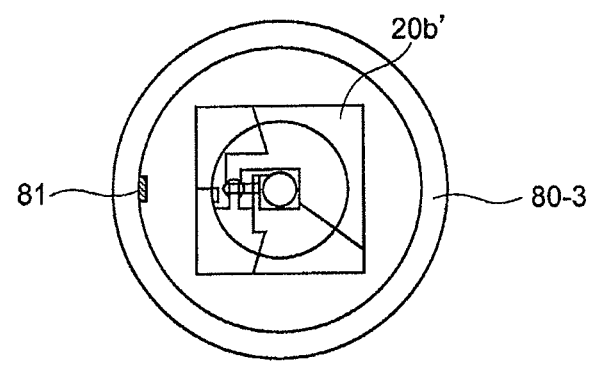
FIG. 13A shows a blood sensor with an attaching guide.

FIG. 13A shows blood sensor 20b' with holder 80-3. Blood sensor 20b' is the same as the blood sensor shown in FIG. 6, is a quadrangle, and has four connection terminals 28a to 31a deriving from four electrodes 28 to 31 of the electrode system. Contact parts 28g to 31g are arranged in connection terminals 28a to 31a, and further, reference contact part 30h, which serves as a reference terminal, is arranged in connection terminal 30a. In addition, holder 80-3 has one attaching guide 81 in its inner periphery.

Figure 13B:
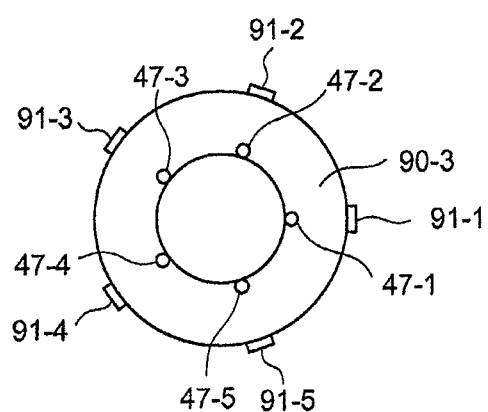
FIG. 13B shows an attaching part of the blood test apparatus to which the blood sensor shown in FIG. 13A is attached.

FIG. 13B shows attaching part 90-3 of the blood test apparatus to which blood sensor 20b with holder 80-3 is attached. Attaching part 90-3 shown in FIG. 13B has five connectors 47-1 to 47-5 and five attaching guides 91-1 to 91-5 on the outer surface of attaching part 90-3. Each of connectors 47 and attaching guides 91 of attaching part 90-3 are preferably arranged at equiangular intervals on the circle line.

It is also possible to form five attaching guides 81 on the inner surface of holder 80-3 and one attaching guide 91 on the outer surface of attaching part 90-3.

Figure 13C:
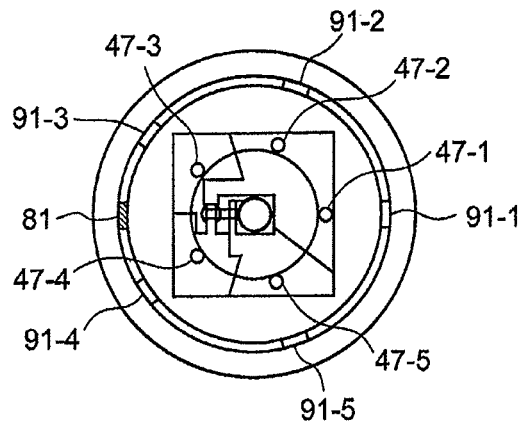
FIG. 13C shows a state where the blood sensor is attached to the attaching part, which prevents the blood sensor from being attached at undesirable positions.
Figure 13D:
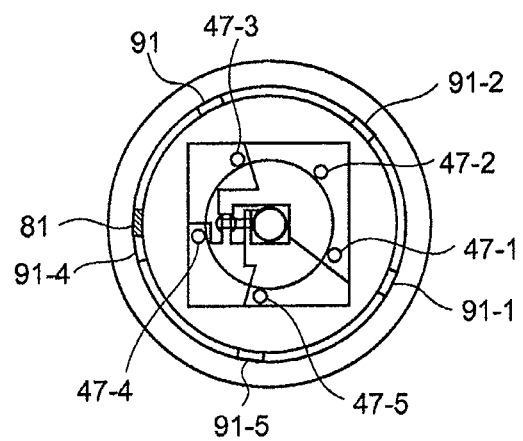
FIG. 13D shows a state where the blood sensor is attached to the attaching part which prevents the blood sensor from being attached at undesirable positions.

FIG. 13C and FIG. 13D show a state where blood sensor 20b' with holder 80-3 is attached to attaching part 90-3 of the blood test apparatus. Four connectors (47-1 or 47-2, 47-3, 47-4 and 47-5 in the figure) out of five connectors 47 of attaching part 90-3 contact with contact parts 28g to 31g of connection terminals 28a to 31a, respectively, and the remaining one connector (47-2 or 47-1 in the figure) contacts with reference contact part 30h. As shown in FIG. 13C and FIG. 13D, projection 81 on the inner surface of holder 80-3 and attaching guides 91 on the outer surface of attaching part 90-3 are defined by each other and prevents connectors 47 of attaching part 90-3 from contacting with the boundaries between the connection terminals of the blood sensor.

Figure 14A:
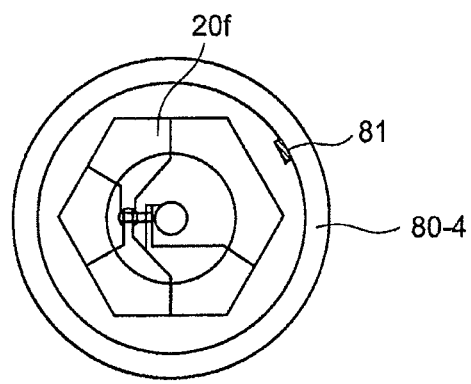
FIG. 14A shows a blood sensor with an attaching guide.

FIG. 14A shows blood sensor 20f with holder 80-4. Blood sensor 20f is the same as the blood sensor shown in FIG. 10, is a hexagon, and has four connection terminals 28a to 31a deriving from the four electrodes of the electrode system and electrode 33. Contact parts 28g to 31g are arranged in connection terminals 28a to 31a, respectively, and, further, contact part 33h, which serves as a reference terminal, is arranged in electrode 33. In addition holder 80-4 has one attaching guide 81 in its inner periphery.

Figure 14B:
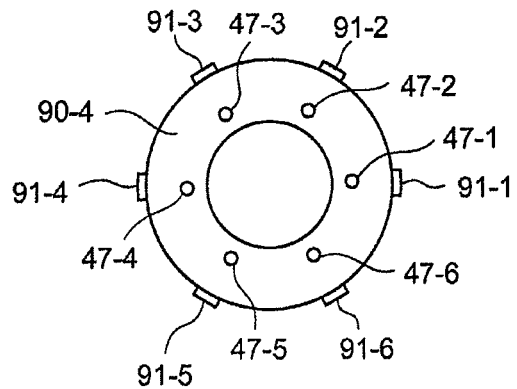
FIG. 14B shows an attaching part of the blood test apparatus to which the blood sensor shown in FIG. 14A is attached.

FIG. 14B shows attaching part 90-4 of the blood test apparatus to which blood sensor 20f with holder 80-4 is attached. Attaching part 90-4 shown in FIG. 14B has six connectors 47-1 to 47-6, and attaching part 90-4 has six attaching guides 91-1 to 91-6 on the outer surface of the attaching part. Each of connectors 47 and a projecting part of attaching part 90-4 are preferably arranged at equiangular intervals on the circle line.

It is also possible to form six attaching guides 81 on the inner surface of holder 80-4 and one attaching guide 91 on the outer surface of attaching part 90-4.

Figure 14C:
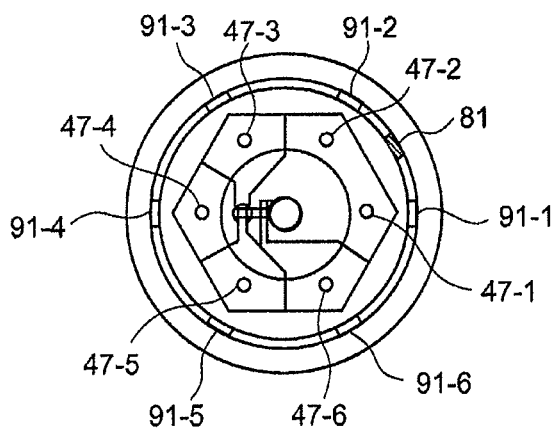
FIG. 14C shows a state where the blood sensor is attached to the attaching part, which prevents the blood sensor from being attached at undesirable positions.
Figure 14D:
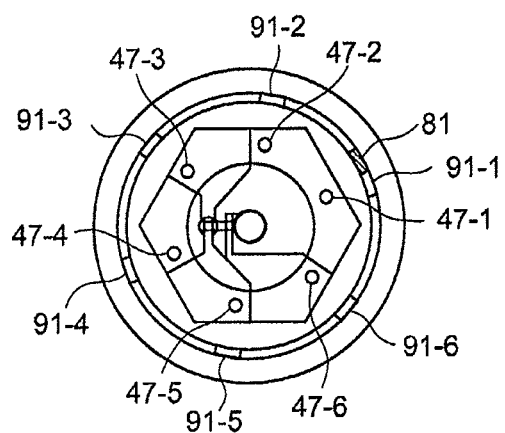
FIG. 14D shows a state where the blood sensor is attached to the attaching part, which prevents the blood sensor from being attached at undesirable positions.

FIG. 14C and FIG. 14D show a state where blood sensor 20f with holder 80-4 is attached to attaching part 90-4 of the blood test apparatus. Four connectors (47-3 to 47-6) out of six connectors 47 of attaching part 90-4 contact with contact parts 28g to 31g of connection terminals 28a to 31a, respectively, and the remaining two connectors (47-1 and 47-2) contact with two reference contact parts 33h and 33h', respectively.

As shown in FIG. 14C and FIG. 14D, projection 81 on the inner surface of holder 80-4 and attaching guides 91 on the outer surface of attaching part 90-4 are defined by each other and prevent connectors 47 from contacting with the boundaries between the connection terminals of blood sensor 20f.

The resistance between two reference terminals 33h and 33h' becomes zero, and so reference terminals can be specified, and, further the connection terminals can be specified.

Figure 15A:
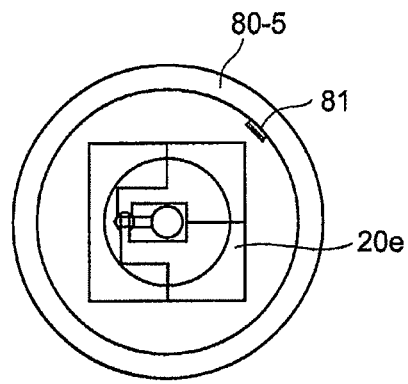
FIG. 15A shows a blood sensor with an attaching guide.

FIG. 15A shows blood sensor 20e with holder 80-5. Blood sensor 20e is the same as the blood sensor shown in FIG. 9A, is a quadrangle, and has connection terminals 28a to 30a deriving from three electrodes 28 to 30 of the electrode system. Contact parts 28g to 30g are arranged in connection terminals 28a to 30a, respectively, and, further, reference contact part 29h which serves as a reference terminal, is arranged in connection terminal 29a. On the other hand, holder 80-5 is fixed and arranged so as to surround blood sensor 20e and has one attaching guide 81 in its inner periphery.

Figure 15B:
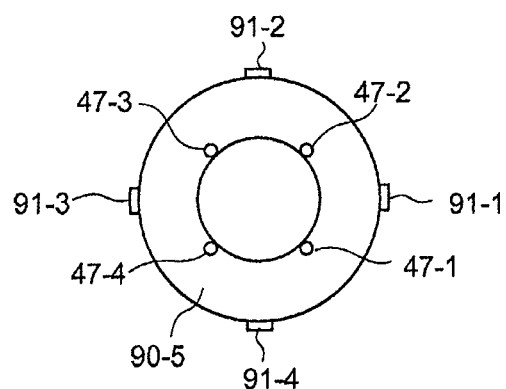
FIG. 15B shows an attaching part of the blood test apparatus to which the blood sensor shown in FIG. 15A is attached.

FIG. 15B shows attaching part 90-5 of the blood test apparatus to which blood sensor 20e with holder 80-5 is attached. Attaching part 90-5 has four connectors 47-1 to 47-4 and four attaching guides 91-1 to 91-4 on the outer surface. Each of connectors 47 and attaching guides 91 of attaching part 90-5 are preferably arranged at equiangular intervals on the circle line.

Figure 15C:
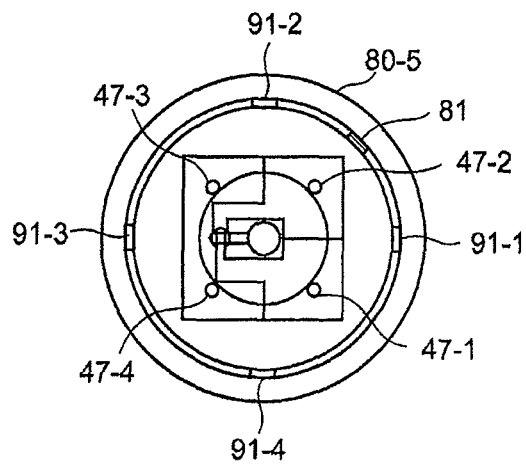
FIG. 15C shows a state where the blood sensor is attached to the attaching part, which prevents the blood sensor from being attached at undesirable positions.
Figure 15D:
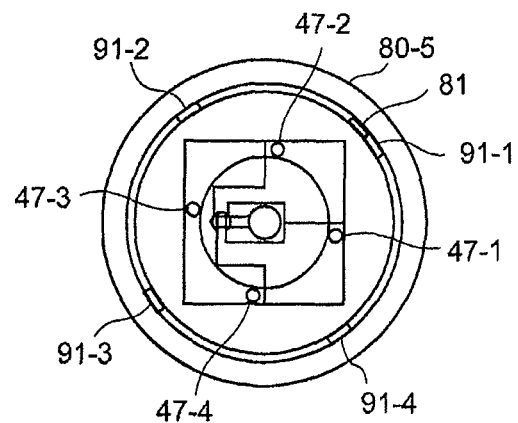
FIG. 15D shows a state where the blood sensor is attached to the attaching part, which prevents the blood sensor from being attached at undesirable positions.

FIG. 15C and FIG. 15D show a state where blood sensor 20e with holder 80-5 is attached to attaching part 90-5 of the blood test apparatus. Three connectors (47-1, 47-2 and 47-3 or 47-4) out of four connectors 47 of attaching part 90-5 contact with contact parts 28g to 30g of connection terminals 28a to 30a, respectively, and the remaining one connector (47-4 or 47-3) contacts with reference contact part 29h.

As shown in FIG. 15C and FIG. 15D, attaching guide 81 on the inner surface of holder 80-5 and attaching guides 91 on the outer surface of attaching part 90-5 are defined by each other, so that it is possible to prevent connectors 47 of attaching part 90-5 from contacting with the boundaries between the connection terminals of blood sensor 20f.

Figure 16A:
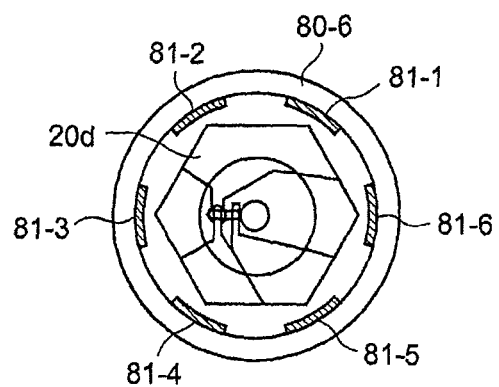
FIG. 16A shows a blood sensor with attaching guides.

FIG. 16A shows blood sensor 20d with holder 80-6. Blood sensor 20d is the same as the blood sensor shown in FIG. 8, is a hexagon, and has four connection terminals 28a to 31a deriving from four electrodes 28 to 31 of the electrode system and dummy electrode 33. Contact parts 28g to 31g are arranged in connection terminals 28a to 31a, respectively, contact part 33g is arranged in dummy electrode 33, and, further, reference contact part 33h, which serves as a reference terminal, is arranged in connection terminal 30a. In addition, holder 80-6 has six attaching guides 81-1 to 81-6 in its inner periphery. Attaching guides 81 are arranged at equiangular intervals and have the same shape.

Figure 16B:
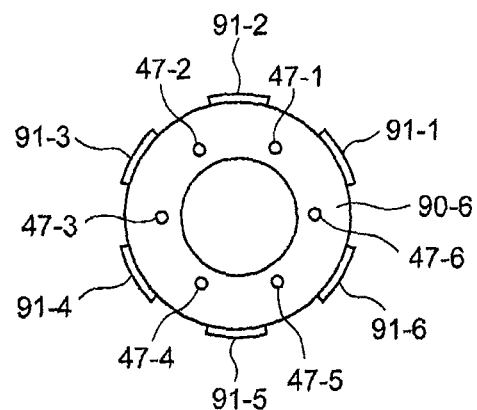
FIG. 16B shows an attaching part of the blood test apparatus to which the blood sensor shown in FIG. 16A is attached.

FIG. 16B shows attaching part 90-6 of the blood test apparatus to which blood sensor 20d with holder 80-6 is attached. Attaching part 90-6 shown in FIG. 16B has six connectors 47-1 to 47-6, and attaching part 90-6 has six attaching guides 91-1 to 91-6 on the outer surface of the attaching part. Attaching guides 91 of attaching part 90-6 are all arranged at equiangular intervals and have the same shape.

Figure 16C:
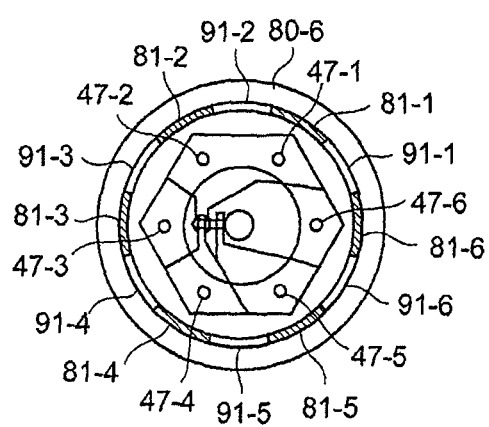
FIG. 16C shows a state where the blood sensor is attached to the attaching part and the attaching guides lead the blood sensor to a predetermined attachment position.
Figure 17A:
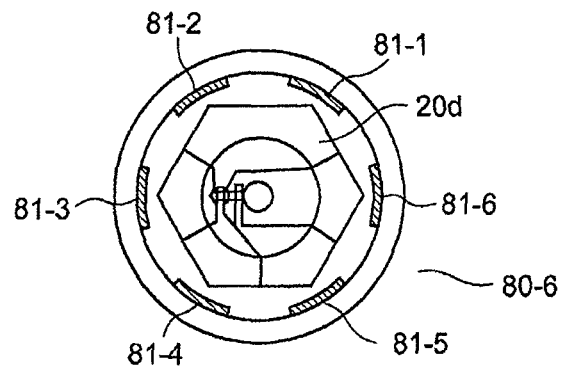
FIG. 17A shows a blood sensor with attaching guides.
Figure 17B:
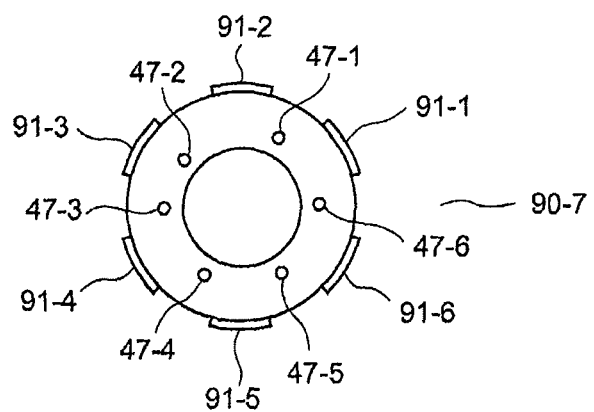
FIG. 17B shows an attaching part of the blood test apparatus to which the blood sensor shown in FIG. 17A is attached, and in which connectors are arranged at unequiangular intervals.
Figure 17C:
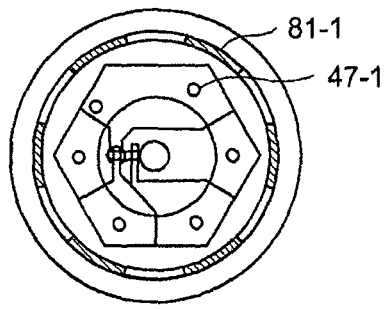
FIG. 17C shows a state where the blood sensor shown in FIG. 17A is attached to the attaching part shown in FIG. 17B.
Figure 17D:
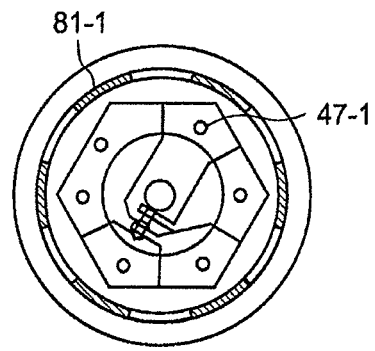
FIG. 17D shows a state where the blood sensor shown in FIG. 17A is attached to the attaching part shown in FIG. 17B.
Figure 17E:
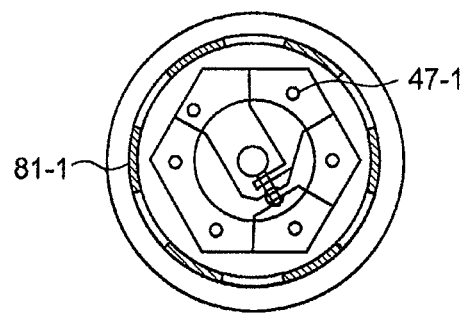
FIG. 17E shows a state where the blood sensor shown in FIG. 17A is attached to the attaching part shown in FIG. 17B.
Figure 17F:
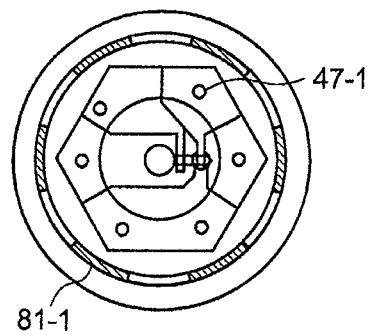
FIG. 17F shows a state where the blood sensor shown in FIG. 17A is attached to the attaching part shown in FIG. 17B.
Figure 17G:
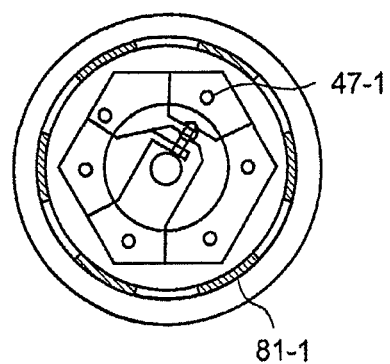
FIG. 17G shows a state where the blood sensor shown in FIG. 17A is attached to the attaching part shown in FIG. 17B.
Figure 17H:
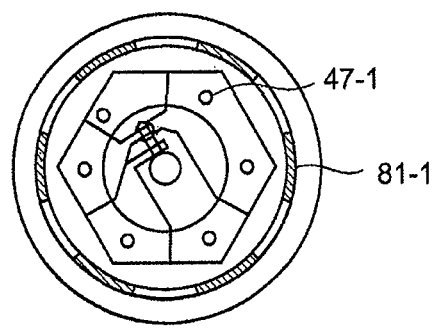
FIG. 17H shows a state where the blood sensor shown in FIG. 17A is attached to the attaching part shown in FIG. 17B.

FIG. 16C shows a state where blood sensor 20d with holder 80-6 is attached to attaching part 90-6 of the blood test apparatus. Attaching guides 81 on the inner surface of holder 80-6 and attaching guides 91 on the outer surface of attaching part 90-6 are engaged and fixed, and thereby blood sensor 20d is attached to attaching part 90-6. Attaching guides 81 and attaching guides 91 are arranged at equiangular intervals and have the same shape, so that attaching guide 81 and attaching guide 91 can be engaged with each other at six positions (see FIG. 17C to FIG. 17H). Upon attachment, four connectors (47-1 or 47-2, 47-3, 47-4 and 47-5) out of six connectors 47 of attaching part 90-6 contact with contact parts 28g to 31g of connection terminals 28a to 31a, one connector (47-2 or 47-1) contacts with reference contact part 30h, and the remaining one connector (47-6) contacts with contact part 33g of dummy electrode 33.

As shown in FIG. 16, compared to a case where a holder that prevents the blood sensor from being arranged at undesirable parts (parts that contact with the boundaries between the connection terminals) as shown in FIG. 10 to FIG. 15, use of a holder that attaches blood sensor 20 at a predetermined position selectively can provide the following advantages.

(1) Even if connectors 47 of attaching part 90 of the blood test apparatus are not arranged on the same circle, it is possible to bring the connectors into contact with connection terminals and reference terminal.

(2) Even if connectors 47 of attaching part 90 of the blood test apparatus are not arranged at equiangular intervals, it is possible to bring the connectors into contact with connection terminals and reference terminal.

FIG. 17 shows (six types of) states where blood sensor 20d (FIG. 17A: the same as FIG. 16A) is attached to attaching part 90-7 (FIG. 17B) with connectors 47-1 to 47-6 arranged not at equiangular intervals but at unequiangular intervals (FIG. 17C to FIG. 17H). Even if the blood sensor is attached in any of the states, connectors 47-1 to 47-6 of attaching part 90-7 contact with predetermined parts in blood sensor 20d.

As described above, a plurality of connectors of the blood test apparatus may contact and connect with the connection terminals and reference terminal of the blood sensor directly, or may connect through wiring. For example, as described later, the blood sampling cartridge may be configured with the blood sensor and the holder in an integrated manner and wirings from the connection terminals and reference terminal of the blood sensor may be installed in the holder. The connectors of the blood test apparatus may be connected with the connection terminals and reference terminal of the blood sensor by contacting with the above-described wirings.

[The Blood Sampling Cartridge]

Blood sensor 20 may be configured integrated with the holder, which is part of the blood sampling cartridge. The holder of the blood sampling cartridge may be provided with a function of holder 80 described above.

Figure 18A:
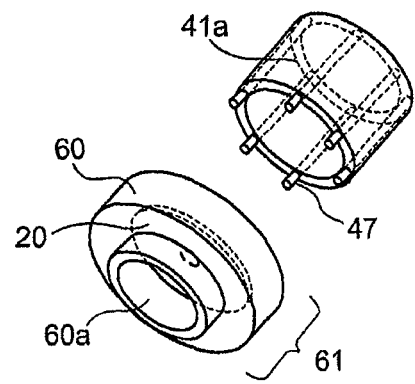
FIG. 18A is a diagrammatic perspective view of a blood sampling cartridge including a blood sensor and a holder, and an attaching part of the blood test apparatus, to which the blood sampling cartridge is attached.

FIG. 18A is a diagrammatic perspective view showing blood sampling cartridge 61 including integrated blood sensor 20 and holder 60, and attaching part 41a (with connectors 47) of the blood test apparatus to which blood sampling cartridge 61 is attached. As shown in FIG. 18A, holder 60 preferably includes projecting part 60a that abuts on the punctured part in addition to blood sensor 20.

Figure 18B:
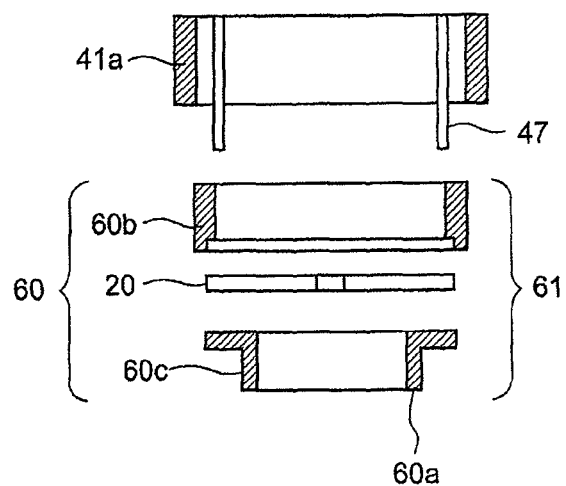
FIG. 18B is a cross-sectional view of a blood sampling cartridge including a blood sensor and a holder, and an attaching part of the blood test apparatus, to which the blood sampling cartridge is attached.

FIG. 18B shows holder 60 divided into first holder 60b and second holder 60c (with projecting part 60a) and blood sampling cartridge 61 including blood sensor 20 sandwiched between first holder 60b and second holder 60c. First holder 60b, second holder 60c and blood sensor 20 may be separable from each other. Blood sampling cartridge 61 is attached to attaching part 41a (with connectors 47) of the blood test apparatus.

Figure 18C:
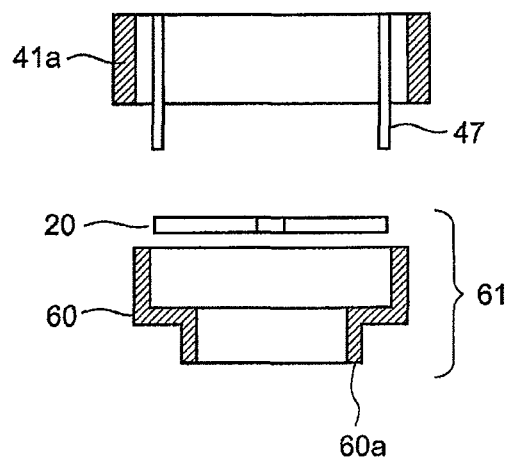
FIG. 18C is a cross-sectional view of a blood sampling cartridge including a blood sensor and a holder, and an attaching part of the blood test apparatus, to which the blood sampling cartridge is attached.
Figure 18D:
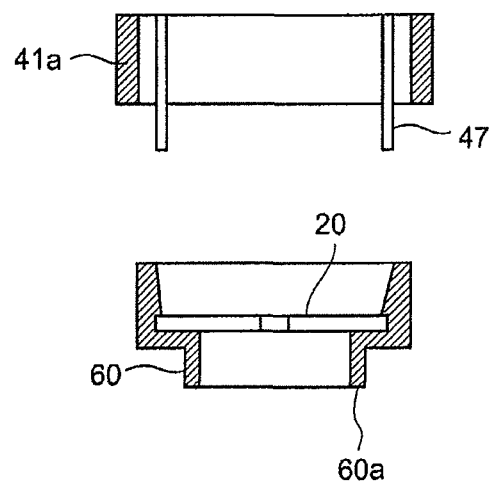
FIG. 18D is a cross-sectional view of a blood sampling cartridge including a blood sensor and a holder, and an attaching part of the blood test apparatus, to which the blood sampling cartridge is attached.

FIG. 18C shows blood sampling cartridge 61 including holder 60 with projecting part 60a and blood sensor 20 attached to holder 60. Holder 60 and blood sensor 20 may be separable. Blood sampling cartridge 61 is attached to attaching part 41a (with connectors 47) of the blood test apparatus. If holder 60 and blood sensor 20 are separable, the blood sensor can be changed singly, but the steps of manufacturing process may increase. FIG. 18D shows blood sampling cartridge 61 including holder 60 with projecting part 60a and blood sensor 20 which is configured integrated with holder 60 and which cannot be separated. Blood sampling cartridge 61 is attached to attaching part 41a (with connectors 47) of the blood test apparatus.

Figure 19A:
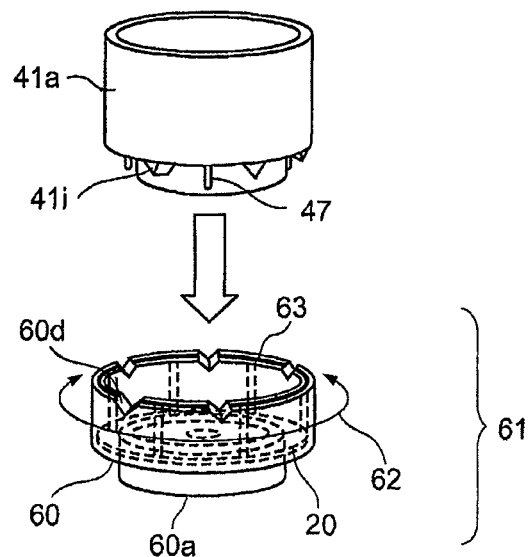
FIG. 19A is a diagrammatic perspective view of a blood sampling cartridge including a blood sensor and a holder, and a blood test apparatus to which the blood sampling cartridge is attached, the blood sampling cartridge having electrodes that connects with the electrodes of the blood sensor through wiring.

FIG. 19A shows blood sampling cartridge 61 having holder 60 with projecting part 60a and blood sensor 20 configured integrated with holder 60. Further, blood sampling cartridge 61 has terminals 63 connected with terminals (such as connection terminals) of blood sensor 20 through wiring 62. Further, holder 60 is provided with concave portion 60d for controlling the attachment position. On the other hand, attaching part 41a of the blood test apparatus to which blood sampling cartridge 61 is attached, has connector 47 and convex portion 41i for controlling the attachment position. Connector 47 is urged by an elastic body such as spring and can be forced into attaching part 41a (see FIG. 19C to FIG. 19E). Convex portion 41i and concave portion 60d are engaged, so that connector 47 can contact with terminal 63.

Figure 19B:
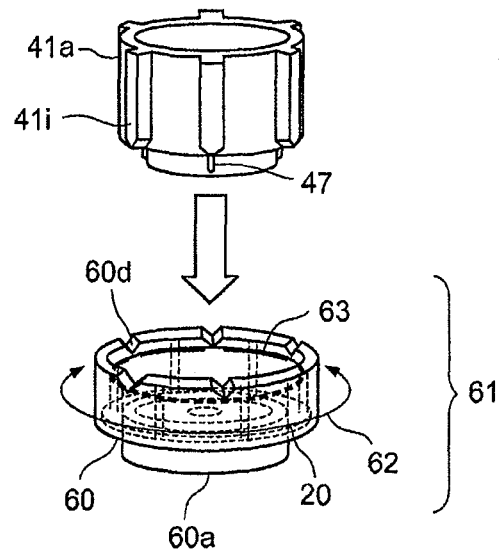
FIG. 19B is a diagrammatic perspective view of a blood sampling cartridge including a blood sensor and a holder, and a blood test apparatus to which the blood sampling cartridge is attached, the blood sampling cartridge having electrodes that connect with the electrodes of the blood sensor through wiring.

Blood sampling cartridge 61 and attaching part 41a shown in FIG. 19B are the same as the blood sampling cartridge and attaching part shown in FIG. 19A except that (1) connector 47 and convex portion 41i in attaching part 41a are not on the same circle and (2) terminal 63 arranged in holder 60 of blood sampling cartridge 61 and concave portion 60*d* are not on the same circle.

Figure 19C:
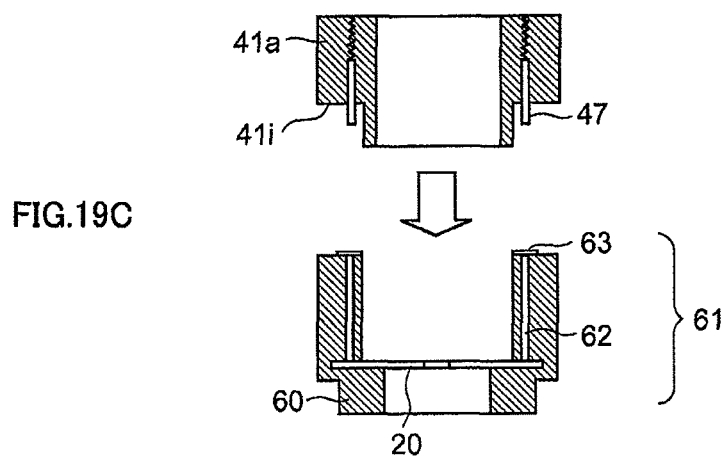
FIG. 19C is a cross-sectional view of a blood sampling cartridge with electrodes that connect with the electrodes of the blood sensor through wiring, and an attaching part of the blood test apparatus.

FIG. 19C is a cross-sectional view of blood sampling cartridge 61 including: holder 60; blood sensor 20 configured integrated with holder 60; wiring 62 from the connection terminals of blood sensor 20 provided inside holder 60; and terminal 63 which is connected with wiring 62 and exposed. Connector 47 of attaching part 41*a* is connected to terminal 63 which is connected with the electrode of blood sensor 20 through wiring 62. Connector 47 of attaching part 41*a* is urged toward the attaching part side (blood sensor side). Connectors 47 may be urged by elastic body 41*j* (such as spring) arranged in attaching part 41*a*.

Figure 19D:
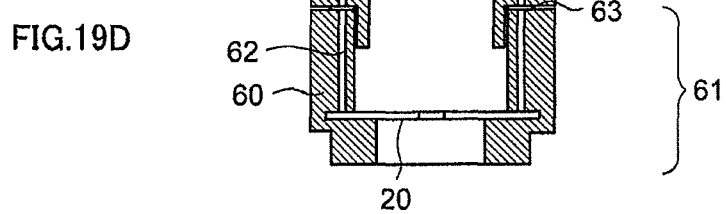
FIG. 19D is a cross-sectional view showing a state where the blood sampling cartridge with electrodes that connect with the electrodes of the blood sensor through wiring, is attached to the attaching part.
Figure 19E:
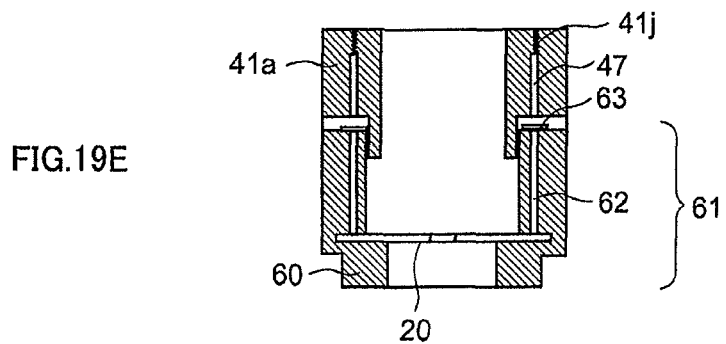
FIG. 19E is a cross-sectional view showing a state where the blood sampling cartridge with electrodes that connect with the electrodes of the blood sensor through wiring, is attached to the attaching part.

FIG. 19D shows a state where blood sampling cartridge 61 is attached to attaching part 41*a* of the blood test apparatus. Concave portion 60*d* of blood sampling cartridge 61 and convex portion 41*i* of attaching part 41*a* are engaged, so that blood sampling cartridge is inserted to an appropriate depth and connector 47 can contact with holder terminal 63. On the other hand, as shown in FIG. 19E, if concave portion 60*d* and convex portion 41*i* are not engaged, connector 47 cannot contact with holder terminal 63.

Figure 20:
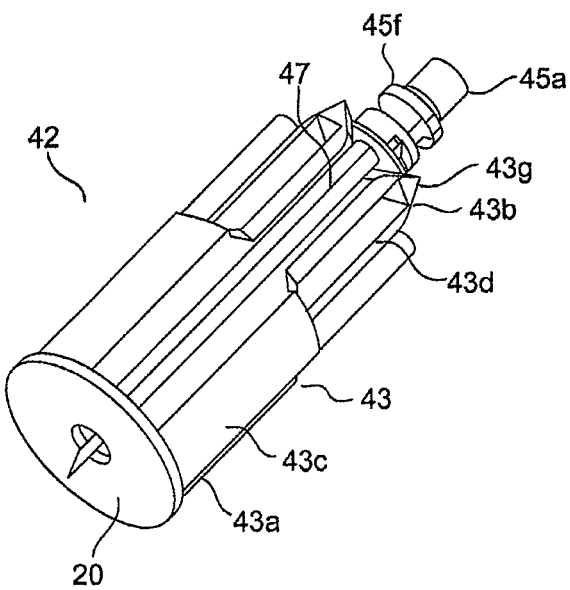
FIG. 20 is a diagrammatic perspective view of the blood sampling cartridge.

FIG. 20 is a diagrammatic perspective view showing an example of a blood sampling cartridge including integrated blood sensor 20, a puncturing means (including a lancet and blood collection needle) and a holder. In blood sampling cartridge 42, the height of cross-shaped convex portion 43*c* formed on the one end 43*a* side (blood sensor 20 side) of holder 43 is higher than the height of cross-shaped convex portion 43*d* formed on the other end 43*b* side of holder 43. That is, holder 43 is thinner at convex portion 43*d* side than at the convex portion 43*c* side. When the front part of the holder of the blood sampling cartridge with respect to the insertion direction is thinner than the rear part as described above, blood sampling cartridge 42 can be inserted into the attaching part of the blood test apparatus in a simple manner. Further, tip end 43*g* (the 43*b* side) of convex portion 43*d* at the other end 43*b* side projects with a sharp angle, and functions as an attaching guide (described above) to the attaching part of the blood test apparatus.

The whole of blood sampling cartridge 42 can be attached to and removed from the attaching part, and so puncturing needle 32 and blood sensor 20 can be attached to and removed from the attaching part together. Therefore, blood sensor 20 and puncturing needle 32 can be attached and changed in a simple manner.

Figure 21:
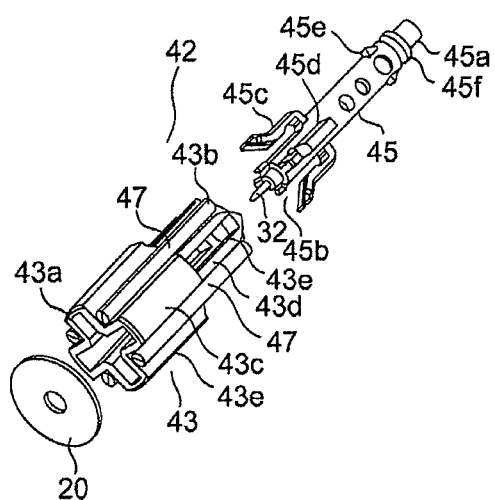
FIG. 21 is a diagrammatic perspective view showing assembly of the blood sampling cartridge.

FIG. 21 is a diagrammatic perspective view of assembly of an example of the blood sampling cartridge. Blood sampling cartridge 42 has: cylinder-shaped holder 43; blood sensor 20 that is attached to one end 43*a* of holder 43; lancet 45 that can slide inside holder 43 freely; and needle 32 that is attached to the other end 45*b* of lancet 45. Connector 47 is preferably in the blood test apparatus. For example, eight connectors (four pairs of connectors) in the case of blood sensor 20*a*, five connectors in the case of blood sensor 20*b*, 20*b*' or 20*c*, six connectors in the case of blood sensor 20*d* or 20*f*, and four connectors in the case of blood sensor 20*e*, are arranged in the blood test apparatus.

Blood sensor 20 is attached to one end 43*a* of holder 43. The outer surface of holder 43 in FIG. 21 has a cross shape, and connector 47 formed with conductive metal (in the blood test apparatus) is led between cross-shaped convex portion 43*c*. Therefore, four connectors are led to blood sampling cartridge 42.

The other end of holder 43 has another convex portions 43*d* formed integrated with convex portion 43*c*, and convex portion 43*d* has hole 43*e*.

Lancet 45 is inserted into holder 43. Guides 45*c* for preventing reuse, are provided 180 degrees apart from each other in lancet 45. Further, guides 45*d* for improving linear mobility are provided between guides 45*c* 180 degrees apart from each other in lancet 45. Guide 45*d* is provided so as to slide in hole 43*e*. Guide 45*c* and guide 45*d* are formed integrated with lancet 45. Convex portion 45*e* is provided near one end 45*a* of lancet 45, and grip part 45*f* is provided between convex portion 45*e* and one end 45*a*.

Figure 22A:
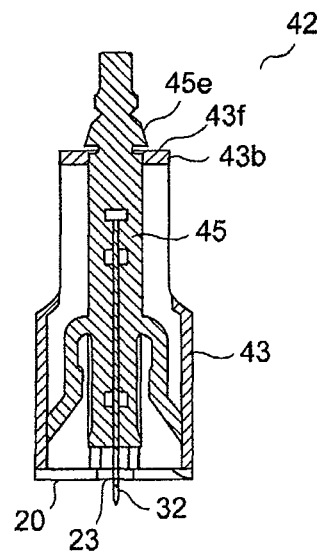
FIG. 22A is a cross-sectional view of the blood sampling cartridge upon puncturing.
Figure 22B:
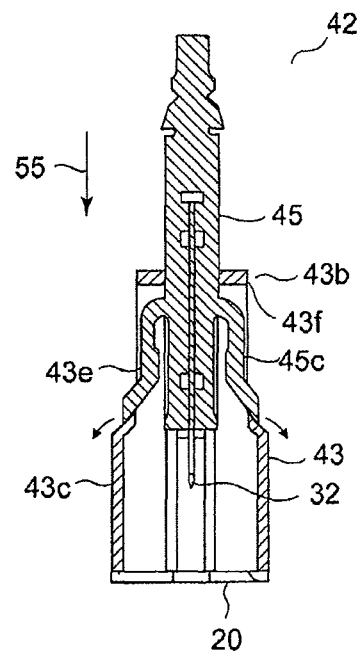
FIG. 22B is a cross-sectional view of the blood sampling cartridge after puncturing is finished.

FIG. 22A is a cross-sectional view of blood sampling cartridge 42 upon puncturing, and FIG. 22B is a cross-sectional view of blood sampling cartridge 42 after puncturing is finished. As shown in FIG. 22A, upon puncturing, puncturing needle 32 projects from blood sensor 20 and stays. At this time, convex portion 45*e* of lancet 45 is latched at latch part 43*f* provided at the other end 43*b* of holder 43. Therefore, puncturing needle 32 does not further project from the blood sensor. As shown in FIG. 22B, when puncturing is finished, puncturing needle 32 is accommodated in holder 43 and stays. The base of guide 45*c* of lancet 45 is latched at latch part 43*f* provided at the other end 43*b* of holder 43. Therefore, lancet 45 does not fall off from holder 43.

In the state shown in FIG. 22B, blood sampling cartridge 42 is removed from attaching part 41*a* of the blood test apparatus. In the state shown in FIG. 22B, even if lancet 45 is pushed in the direction of arrow 55 by error, guide 45*c* runs onto convex portion 43*c* through hole 43*e* of holder 43 by its elasticity. The base of guide 45*c* is then latched at the end of hole 43*e* and stay, and so puncturing needle 32 does not project from blood sensor 20 again so that it is secure and does not make the patient feel fear.

Figure 23:
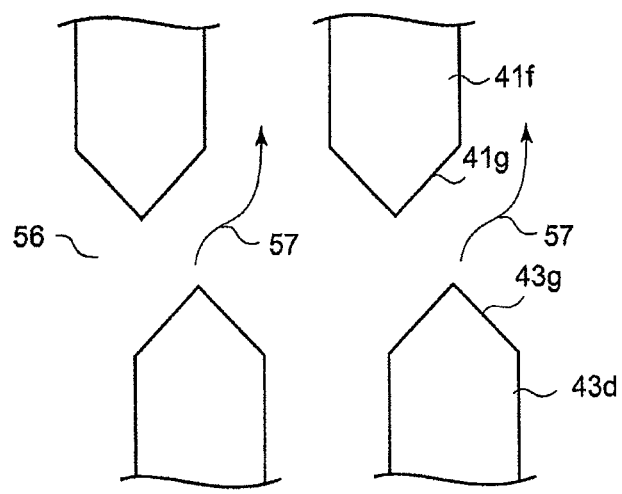
FIG. 23 is a plan view that expands the main part of an attaching guide for inserting the blood sampling cartridge into an attaching part.

As described above, holder 43 of cartridge 42 preferably has a function of an attaching guide for attaching blood sensor 20 to attaching part 41*a* of the blood test apparatus. FIG. 23 is a plan view that expands the main part of an example of the attaching part for attaching cartridge 42 with blood sensor 20 to attaching part 41*a* of the blood test apparatus. Convex portion 43*d* formed in holder 43 functions as attaching guide. Convex portion 41*f* is formed inside attaching part 41*a* of the blood test apparatus. Tip part 41*g* of convex portion 41*f* and tip part 43*g* of convex portion 43*d* preferably have a sharp angle.

When cartridge 42 is attached, convex portion 43*d* and convex portion 41*f* face each other, and, even if the relative position is shifted, cartridge 42 is attached while its angle is modified as shown by arrow 57. As a result, the contact parts arranged in the blood sensor of cartridge 42 and the connectors of the blood test apparatus contact reliably.

Figure 24:
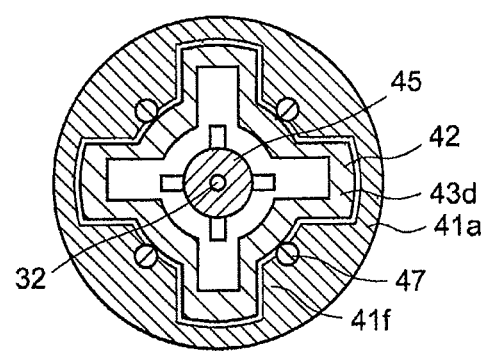
FIG. 24 is a cross-sectional view of the attaching part of the blood test apparatus into which the blood sampling cartridge is inserted.

FIG. 24 is a cross-sectional view of attaching part 41*a* of the blood test apparatus to which cartridge 42 is attached. As shown in FIG. 24, cartridge 42 is attached with the help of the attaching guide, so that convex portion 41*f* and convex portion 43*d* are engaged, the angle of cartridge 42 is modified to a predetermined angle, and cartridge 42 is fixed inside attaching part 41*a*. As a result, connector 47 contacts with the contact part of blood sensor 20 reliably and transmit a signal of blood sensor 20 to measuring circuit 52 reliably.

Figure 25:
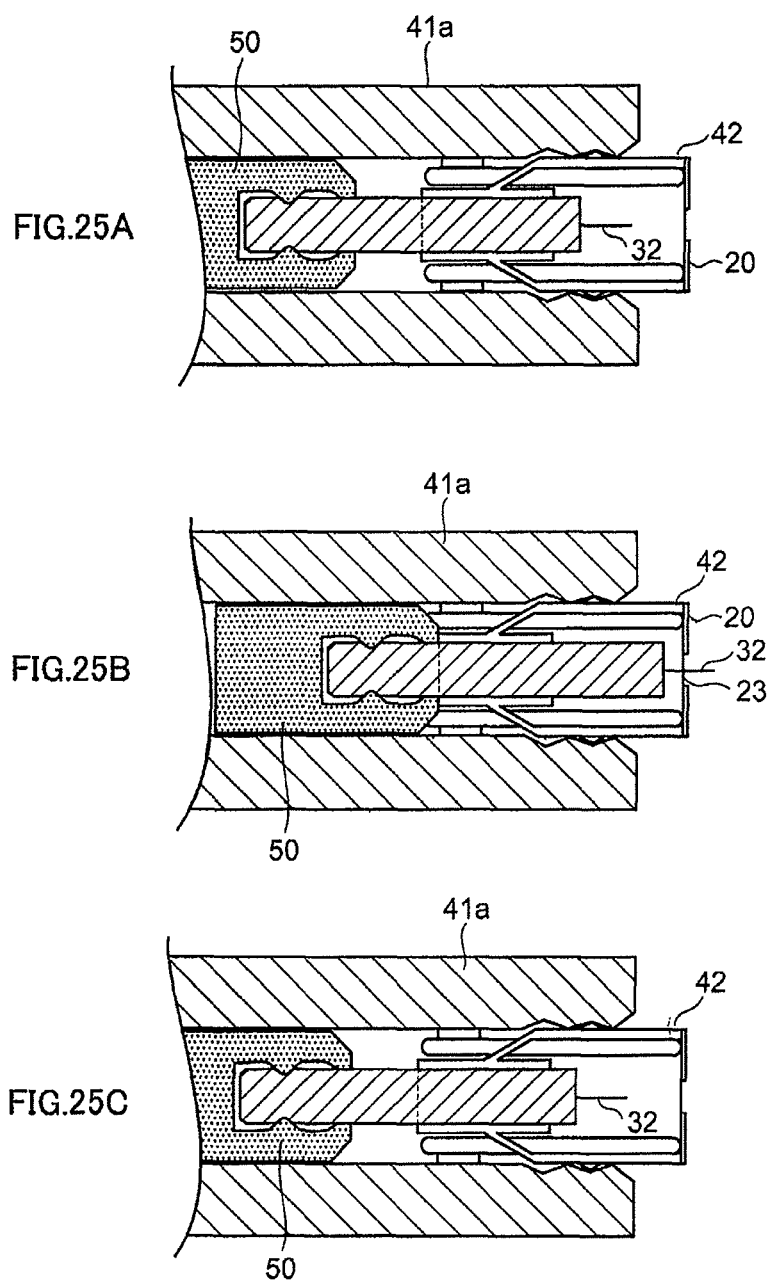
FIG. 25A is a cross-sectional view showing a state of a lancet before puncturing in a state where the blood sampling cartridge is attached to the blood test apparatus.
FIG. 25B is a cross-sectional view showing a state of the lancet upon puncturing in a state where the blood sampling cartridge is attached to the blood test apparatus.
FIG. 25C is a cross-sectional view showing a state of the lancet after puncturing is finished in a state where the blood sampling cartridge is attached to the blood test apparatus.

FIG. 25 is a cross-sectional view of cartridge 42 and attaching part 41*a* into which this cartridge 42 is inserted. FIG. 25A shows a state where plunger 50 is pulled backward, and puncturing needle 32 is in cartridge 42. That is, FIG. 25A shows a state before puncturing. FIG. 25B shows a state where plunger 50 projects forward, and puncturing needle 32 breaks through cover 23 of sensor 20 and punctures the skin of the patient. FIG. 25C shows a state where plunger 50 is pulled backward, and puncturing needle 32 is accommodated in cartridge 42. In this way, except for the state where plunger 50 projects forward, puncturing needle 32 is accommodated in cartridge 42.

[The Blood Test Apparatus]

Figure 26:
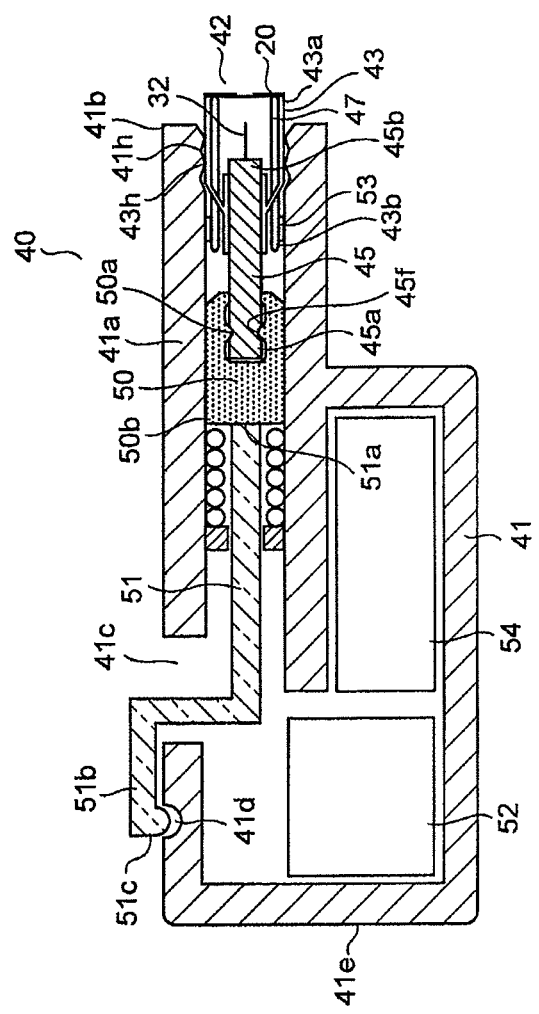
FIG. 26 is a cross-sectional view of the blood test apparatus to which the blood sampling cartridge is attached.

An example of the blood test apparatus to which blood sensor 20 is attached will be described. FIG. 26 is a cross-sectional view of blood test apparatus 40. Blood test apparatus 40 has housing 41 formed with resin. Housing 41 is a frame of the apparatus and accommodates main members of the apparatus.

One side of housing 41 is attaching part 41a. Blood sampling cartridge 42 is preferably inserted into end 41b of attaching part 41a. Positioning concave portion 41h provided on the attaching part 41a side and positioning convex portion 43h provided at holder 43 on the blood sampling cartridge 42 side are engaged, and thereby blood sampling cartridge 42 inserted to attaching part 21a is fixed to a predetermined position in attaching part 41a (position in a horizontal direction in FIG. 26).

Blood sampling cartridge 42 has: cylinder-shaped holder 43; blood sensor 20 that is attached to one end 43a of holder 43; lancet 45 that can slide inside holder 43 freely; and puncturing needle 32 that is attached to the other end 45b of lancet 45. Blood sensor 20 includes electrodes and connection terminals connected to the electrodes. Connector 47 contacts with the connection terminal.

Grip part 45f formed near one end 45a of lancet 45 which is one member of blood sampling cartridge 42, is held by holding part 50a provided at one end of plunger 50 that slides inside attaching part 41a. Plunger 50 holds lancet 45, so that, when the skin is punctured with puncturing needle 32, puncturing needle 32 does not shake and enables high linearity of movement, so that it is possible to puncture the skin with puncturing needle 32 stably.

On the other hand, the other end 50b of plunger 50 is connected to one end 51a of handle 51 formed in the shape of a crank. Latch convex portion 51c is formed at the other end 51b of handle 51. Handle 51 goes through hole 41c formed in housing 41 and is latched by the joint of latch convex portion 51c and latch concave portion 41d.

As the drive mechanism of plunger 50, for example, the method disclosed in Japanese Patent Application Laid-Open No. 2006-314718 can be adopted. According to this method, a puncturing needle can move straight backward and stay after puncturing, so that it is possible to alleviate the pain of the patient upon puncturing to a minimum, and, further, accomplish a mechanism for preventing the blood collection needle from puncturing the patient's skin several times and adjusting the depth of puncturing, in a simple manner. By providing such a prevention mechanism and an adjustment mechanism on the blood test apparatus, instead of providing on the blood sampling cartridge, it is possible to realize a smaller and lower-cost blood sampling cartridge.

An example of the mechanism for preventing a puncturing needle from puncturing the patient's skin several times, is disclosed in Japanese Patent Application Laid-Open No. 2006-314718. A pull string, one end of which is fixed, has the other end hooked on a lever for which rotation is partially limited and which is provided in the plunger. A forward force is given to the plunger by a contracting and restoring force of the pull string. The plunger passes the position where the forward force is no longer given then the plunger moves on by inertia. In this case, the pull string is extended again with the help of the lever as fulcrum, and the plunger is given a force towards the rear end by the restoring force of the pull string.

In this way, by configuring an urging means that gives a force towards the front end and a force towards the rear end to the plunger, with one pull spring, manufacturing process of a puncturing tool is simplified and a puncturing needle is prevented from puncturing the patient's skin several times (see unexamined patent publication).

Figure 34:
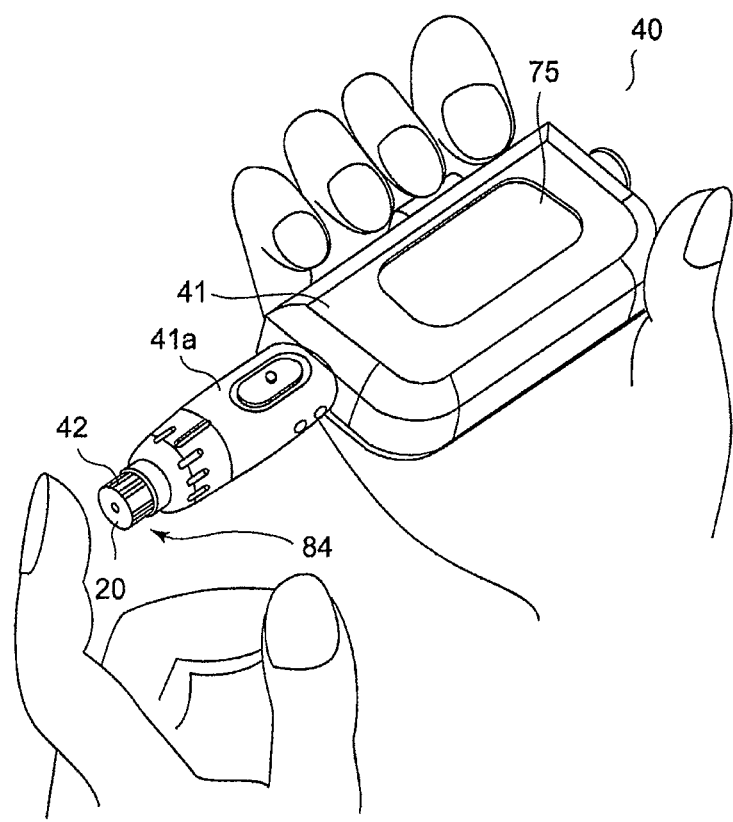
FIG. 34 shows a state of use of the blood test apparatus.
Figure 35:
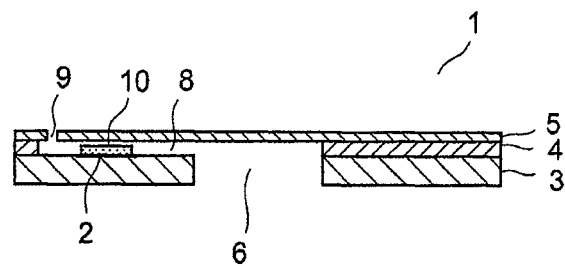
FIG. 35 is a cross-sectional view of a conventional blood sensor.
Figure 36A:
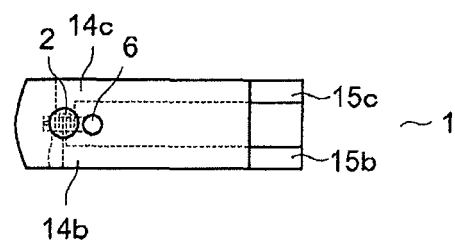
FIG. 36A and FIG. 36B are perspective plan views of a conventional blood sensor.
Figure 36B:
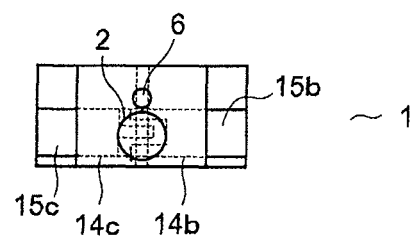
Figure 37:
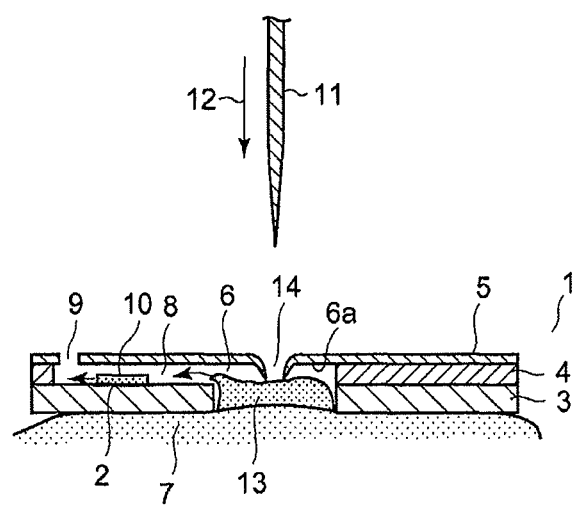
FIG. 37 illustrates the way to use a conventional blood sensor.

As an example of the mechanism for adjusting the depth of puncturing, when the plunger moves in the direction of the axis, puncturing depth adjusting knob 84 that limits the amount of move and that has a receiving part, is jointed rotatably (see FIG. 34). The receiving part (not shown) of puncturing depth adjusting knob 84 has a helical shape. By rotating adjusting knob 84 with respect to attaching part 41a of housing 41, it is possible to change the amount of move of the plunger in the direction of the axis.

Measuring circuit 52 is accommodated inside the other end 41e side of housing 41. Measuring circuit 52 is connected to terminal 53 formed in attaching part 41a. Further, terminal 53 is connected to connector 47. Terminal 53 is configured with two or more (usually, four or five) terminals 53a to 53d (or 53e) and connected to matching connectors 47a to 47d (or 47e). As described above, connectors 47 contact with matching connection terminals, respectively. The housing accommodates battery 54 that supplies power to measuring circuit 52.

As described above, blood test apparatus 40 has blood sampling cartridge 42 that is integrated with built-in lancet 45 with puncturing needle 32 attached and built-in blood sensor 20, and blood sampling cartridge 42 can be attached to and removed from attaching part 41a. Therefore, the whole of blood sampling cartridge 42, including the puncturing needle and the blood sensor, can be changed in a simple manner. Further, blood sensor 20 and puncturing needle 32 are changed together every test, so that there is no fear that puncturing needle 32 is used several times and there is no threat of infection.

Puncturing needle 32 of blood sampling cartridge 42 is accommodated in holder 43 upon attachment, so that puncturing needle 32 does not hurt the patient and is secure and does not make the patient feel fear. Further, puncturing needle 32 accommodated in holder 43 does not allow direct touch, and so is sanitary.

[The Flow of the Blood Test]

Figure 27:
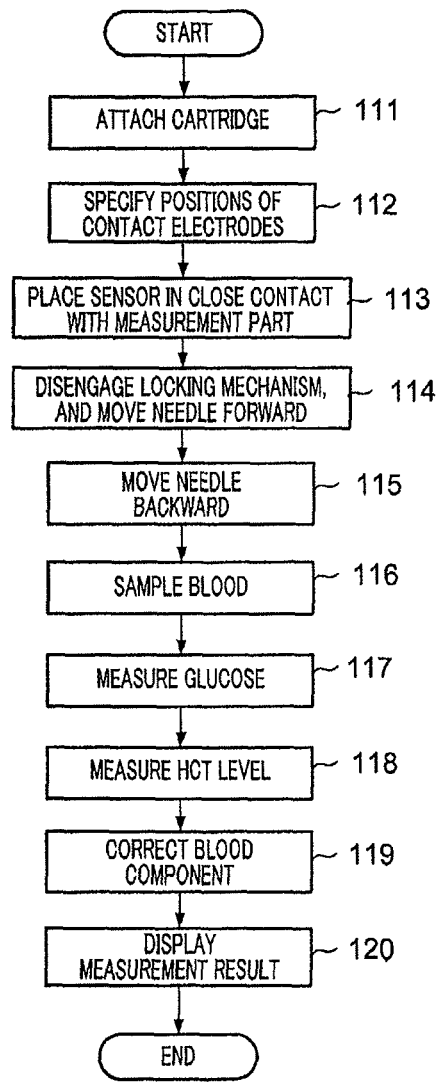
FIG. 27 shows a flow of blood sugar level (glucose) measurement using the blood test apparatus.

FIG. 27 shows an example of the flow of the test using blood test apparatus 40. In step 111, blood sampling cartridge 42 is inserted to attaching part 41a and attached to blood test apparatus 40. By this insertion, holder 43 is pressed into attaching part 41a and latched, and positioning concave portion 41h and positioning convex portion 43h are jointed to determine the position. Further, grip part 45f of lancet 45 is held by holding part 50a of plunger 50.

In step 112, the connection terminals of blood sensor 20 are specified. For example, in the case of blood sensor 20a, resistance values between the contact parts in pairs (between 28c to 31c and 28d to 31d) are measured, and reference terminal 29f is specified. Based on specified reference terminal 29f, connection terminals 28a to 31a are specified. As a result, electrodes 28 to 30 of the electrode system are also specified.

In step 113, the patient's skin is pressed with blood sensor 20 of blood sampling cartridge 42 and blood sensor 20 is placed in close contact with the patient's skin. In step 114, a locking mechanism of plunger 50, formed by latch convex portion 51c provided at handle 51 and latch concave portion 41d provided at housing 41, is disengaged. By this means, puncturing needle 32 attached to lancet 45 projects toward the skin by plunger 50 urged by the spring.

In step 115, after the patient's skin is punctured with puncturing needle 32, puncturing needle 32 is moved backward and accommodated inside blood sampling cartridge 42. In step 116, blood flows out and is sampled. The blood flowing out is brought to blood sensor 20 and led to detecting section 27 placed inside supply channel 25. After electrode 29 as a detecting electrode determines that blood of the amount necessary for measurement is led to the detecting section, sampling blood is finished. In this way, blood is not over-sampled, so that it is possible to alleviate the load on the patient significantly. When blood 13 is not detected at detecting section 27 after a predetermined time has passed or when the amount of blood 13 is not adequate, a warning means may be activated for warning, and the measure may be displayed on a display section.

In step 117, the glucose in the sampled blood is measured. After the glucose in the blood and a glucose oxidation-reduction enzyme are reacted for a certain period, a voltage is applied between electrode 28 as a working electrode and electrode 30 as a counter electrode. The mediator in a reduction condition, produced on electrode 28 by enzyme reaction, is oxidized, and its oxidation current is measured. The reaction time of a glucose and an oxidation-reduction enzyme is normally 10 seconds or less, the voltage applies in step 117 is normally 0.2 to 0.5V, and the application time is normally 5 seconds or less. This application time is measured by timer 79 (described later).

In step 118, the hematocrit (Hct) level is measured. When a voltage is applied between electrode 31 as a working electrode and electrode 30 as a counter electrode, a current that depends on the Hct level is measured. The Hct level is measured based on the detected current. The measured Hct level is utilized to correct the result of measuring the glucose. The relationship between the current and the Hct level may be calculated in advance as a calibration curve, and the measured current may be applied as it is.

Generally, the voltage applied in step 118 is approximately 2 to 3 V, and the application time is approximately 5 seconds or less. A mediator is not provided at electrode 31, which is a working electrode. There is a certain interval between electrode 31 and electrode 30, and only blood exists in this interval. Therefore, in step 118, an oxidation current that depends on the Hct level can be measured without being influenced by reagent 10.

Then, in step 119, the measurement result of the blood components is corrected. That is, using the Hct level measured in step 118, the glucose content calculated in step 117 is corrected. This correction is performed based on the calibration curve (including a calibration table) created in advance. The corrected glucose content is displayed on display section 75 of blood test apparatus 40.

After going through steps 117, 118 and 119 of blood sugar level measurement, used blood sampling cartridge 42 is collected or discarded every measurement.

[The Principle of Measuring the Blood Sugar Level]

Figure 28:
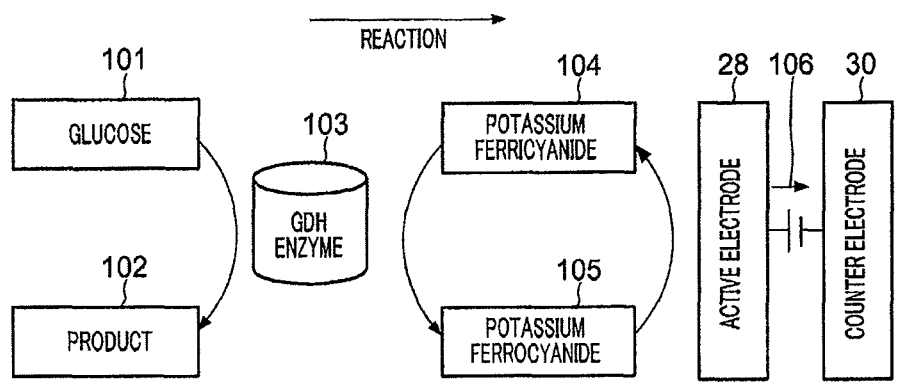
FIG. 28 shows a principle of glucose measurement in blood using the blood test apparatus.

FIG. 28 shows the measurement principle of blood test apparatus 40 that measures the blood sugar level of blood. Glucose 101 in blood reacts with glucose dehydrogenase (GDH) 103 specifically and product 102 is given, and potassium ferricyanide 104 is reduced and potassium ferrocyanide 105 is generated. The amount of generated potassium ferrocyanide 105 is proportional to the concentration of glucose 101. Potassium herrocyanide 105 is oxidized on electrode 28 (see FIG. 4 and the like) as a working electrode, and, at this time, oxidation response current 106 flowing electrode 30 as a counter electrode is proportional to the concentration of glucose 101. Therefore, the blood sugar level can be measured based on this oxidation response current 106.

Figure 29:
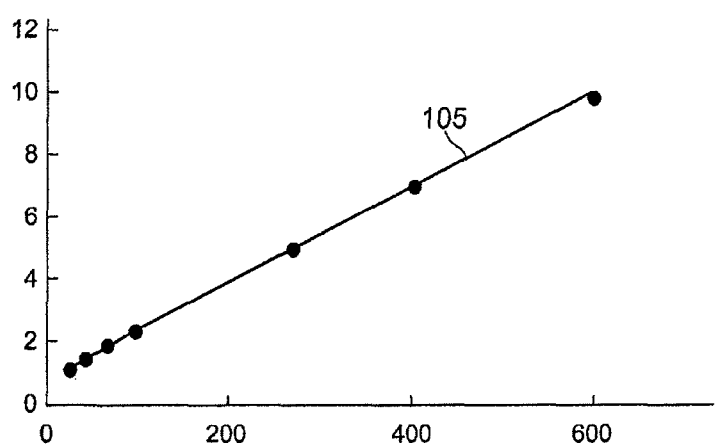
FIG. 29 is a characteristic diagram of blood sugar level (glucose) measurement.

FIG. 29 shows an output example of the measurement result of blood test apparatus 20. The horizontal axis shows the concentration (mg/dL) of glucose 101, and the vertical axis shows response current 106 (µA). In this way, oxidation response current 106 is proportional to the concentration of glucose 101.

[A Block Diagram of the Blood Test Apparatus]

Figure 30:
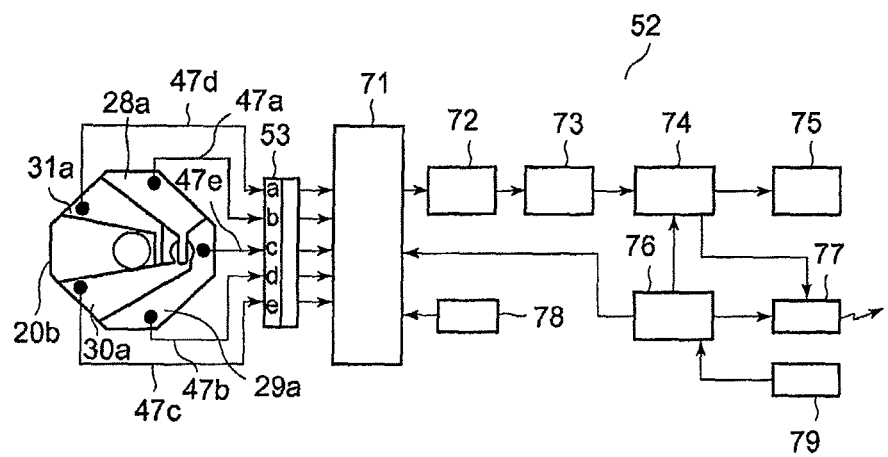
FIG. 30 is a block diagram of the blood test apparatus.

FIG. 30 is a block diagram of blood test apparatus 52. The same components will be assigned the same reference numerals for ease of explanation. Blood test apparatus 52 in FIG. 30 has blood sensor 20b. Connection terminals 28a to 31a and reference terminal 29h of blood sensor 20b are connected to terminals 53a to 53e via connectors. Terminals 53a to 53e are connected to switch circuit 71, and the output of switch circuit 71 is connected to the input of current/voltage converter 72. The output of current/voltage converter 72 is connected to the input of calculating section 74 via analogue/digital converter (hereinafter A/D converter) 73. The output of calculating section 74 is connected to display section 75 (for example, a liquid crystal display device) and also connected to the input of transmitting section 77. Further, reference voltage supply 78 is connected to switch circuit 71. Reference voltage supply 78 may be a ground potential. The output of controlling section 76 is connected to a control terminal of switch circuit 71, calculating section 74, transmitting section 77 and timer 79. A warning means (not shown) may be connected to the output of controlling section 76.

When a test is conducted using blood test apparatus 52 adopting blood sensor 20b, it is necessary to specify which of terminals 53a to 53e connection terminals 28a to 31a are connected to (via connectors), before measuring the blood components. Therefore, by the command of controlling section 76, out of terminals 33a to 33e, terminals having conductivity with the neighboring terminals are specified. If a terminal having conductivity is specified, the electrode connected to the terminal is determined to be connection terminal 29a. Using the terminal connected to connection terminal 29a as a reference, terminals connected to connection terminals 30a, 31a and 28a, are determined in that order. In this way, after the terminals connected to connection terminals 28a to 31a are determined, the blood components are measured.

Next, switch circuit 71 is switched, and electrode 28 as a working electrode for measuring the amount of blood components is connected to current/voltage converter 72 via terminal 53. On the other hand, electrode 29 which serves as a detecting electrode for detecting the inflow of blood is connected to reference voltage supply 78 via terminal 53. A certain voltage is applied between electrode 28 and electrode 29. When the blood is led to the detecting section in this state, a current flows between electrode 28 and electrode 29. This current is converted to a voltage by current/voltage converter 72, and the voltage value is converted to a digital value by A/D converter 73. The digital value is then outputted to calculating section 74. Calculating section 74 detects the inflow of blood based on the digital value.

Next, the amount of blood components (glucose) is measured. The glucose content is measured by, first, switching switch circuit 71 by the command of controlling section 76 and connecting electrode 28, which is a working electrode for measuring the glucose content, to current/voltage converter 72 via terminal 53. On the other hand, electrode 30, which is a counter electrode for measuring the glucose content, is connected to reference voltage supply 78 via terminal 53.

While the glucose in the blood and the oxidation-reduction enzyme are reacted for a certain period, current/voltage converter 72 and reference voltage supply 78 may be turned off. If a certain voltage (0.2 to 0.5 V) is applied between electrode 28 and 30 by the command of controlling section 76 after the glucose in the blood and the oxidation-reduction enzyme are reacted for a certain period (10 seconds or less), a current flows between electrode 28 and electrode 30. This current is converted to a voltage by current/voltage converter 72, and the voltage value is converted to a digital value by A/D converter 73 and outputted to calculating section 74. Calculating section 74 converts the digital value to a glucose content.

After the glucose content is measured, the Hct level is measured. First, by the command of controlling section 76, switch circuit 71 is switched to connect electrode 31, which is a working electrode for measuring the Hct level, to current/voltage converter 72 via terminal 53. On the other hand, electrode 28, which is a counter electrode for measuring the Hct level, is connected to reference voltage supply 78.

Then, by the command of controlling section 76, a certain voltage (2 to 3 V) is applied between electrode 31 and electrode 28 from current/voltage converter 72 and reference voltage supply 78. The current flowing between electrode 31 and electrode 28 is converted to a voltage by current/voltage converter 72, and the voltage value is converted to a digital value by A/D converter 73 and outputted to calculating section 74. Calculating section 74 measures the Hct level based on the digital value.

Using the measured Hct level and the glucose content, and, with reference to the calibration curve or the calibration table prepared in advance, the glucose content is corrected with the Hct level. The result after correction may be displayed on display section 75 or transmitted to an injection apparatus that injects a curative drug (for example, insulin) from transmitting section 77. The result after correction may be transmitted by radio, but is preferably transmitted using optical communication which does not interfere with medical equipment.

If the injection apparatus for injecting curative drug can set a dose of the curative drug automatically based on the result after correction (measured data) transmitted from transmitting section 77, the patient does not have to set a dose of the curative drug, which eliminates the inconvenience of setting a dose. Further, the amount of insulin can be set for the injection apparatus without involving an artificial means, so that it is possible to prevent setting errors.

[The Negative Pressure Means]

The blood test apparatus of the present invention may have a negative pressure means. By the negative pressure means, a negative pressure is preferably applied near the part of the skin punctured with puncturing needle 32. Therefore, blood test apparatus 40 having the negative pressure means preferably has a member for surrounding the neighborhood of the punctured part of the skin, and may apply a negative pressure to the space surrounded by the member.

Figure 31:
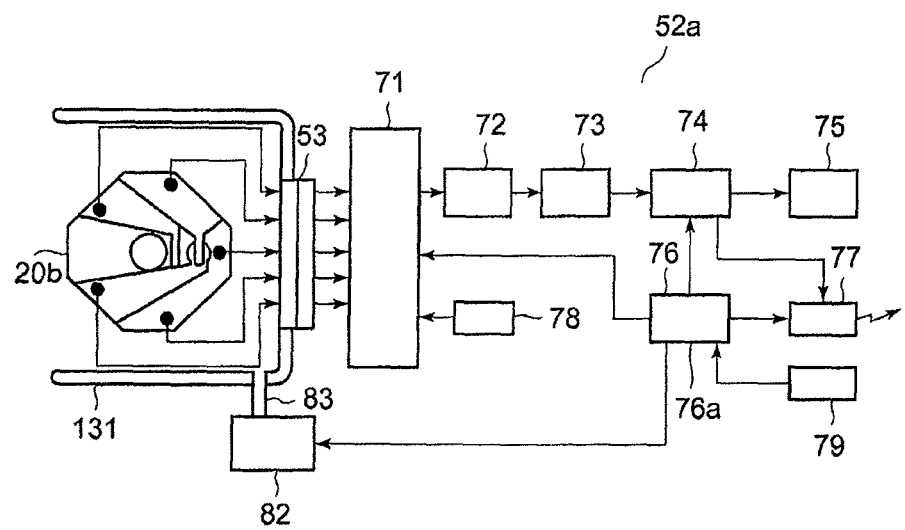
FIG. 31 is a block diagram of the blood test apparatus with a negative pressure apparatus.

FIG. 31 is a block diagram of blood test apparatus 52a having a negative pressure means. Blood test apparatus 52a is different from blood test apparatus 52 shown in FIG. 30 in that blood test apparatus 52 has a negative pressure means, and so the difference will be mainly described. The same components as blood test apparatus 52 will be assigned the same reference numerals for ease of explanation.

In FIG. 31, guard part 131 is provided, which extends from 41b of attaching part 41a. Controlling section 76a is connected to negative pressure means 82 (for example, a vacuum generator), and the output of negative pressure means 82 is connected inside of guard part 131 via negative pressure path 83. Therefore, negative pressure can be supplied inside of guard part 131 by negative pressure means 82.

Negative pressure means 82 may be started after step 111 in which blood sensor 20a is brought into close contact with the measurement part, and stay after step 116 in which blood is sampled. Upon sampling blood, by supplying a negative pressure between the skin punctured with the puncturing needle and blood sensor 20b, the skin is put under a state of tension so as to enable fast and reliable blood sampling.

Figure 32:
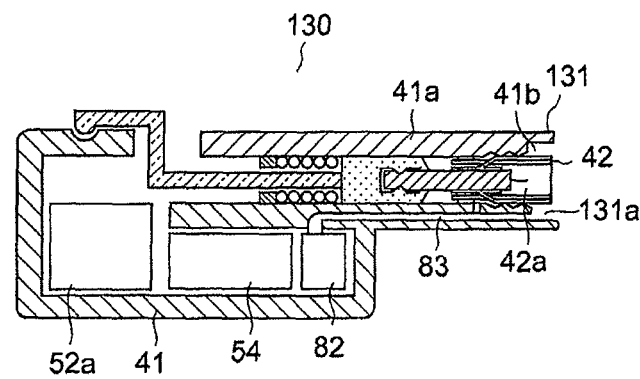
FIG. 32 is a cross-sectional view of the blood test apparatus with a negative pressure apparatus.

FIG. 32 is a cross-sectional view of blood test apparatus 52a. In FIG. 32, guard part 131 is provided which extends from end 41b of attaching part 41a. The output of negative pressure means 82 (for example, a vacuum generator) connected to controlling section 76a is connected inside guard part 131 via negative pressure path 83. Therefore, negative pressure means 82 can supply a negative pressure inside guard part 131.

Figure 33:
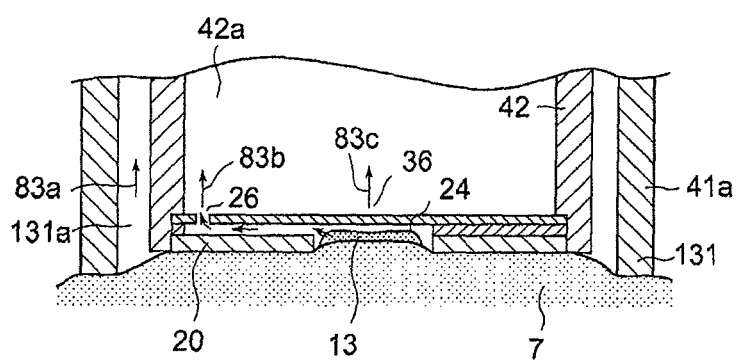
FIG. 33 is a cross-sectional view that expands the main part of the blood test apparatus with a negative pressure apparatus.

FIG. 33 is a cross-sectional view that expands the main part near guard part 131 of blood test apparatus 52a. In FIG. 33, as a result of the operation of negative pressure means 82, inner part 131a of guard part 131 is sucked in as shown by arrow 83a, and skin 7 is brought in close contact with sensor 20 of guard part 131 and put under a state of tension. At this time, inner part 42a of blood sampling cartridge 42 is also sucked in. Before puncturing with puncturing needle 32, skin 7 is preferably lifted by sucking in the inner part of storing part 24 in a direction of arrow 83b by supplying a negative pressure from air hole 26. By this means, skin 7 is put under a state of tension to make puncturing easier. After puncturing with puncturing needle 32, the inner part of storing part 24 is sucked in from puncturing hole 36 in addition to from air hole 26 as shown by arrow 83c, and a negative pressure is further supplied to further lift skin 7 and help blood 13 to be sampled.

In this way, air hole 26 and supply channel 25 are also used as negative pressure supply channels, so that it is possible to supply a negative pressure to the inner part of storing part 24 without providing a negative pressure supply channel separately. Further, after puncturing, puncturing hole 36 can be also used as a negative pressure supply channel.

FIG. 34 shows a state where the patient tries to examine blood using blood test apparatus 40. The patient is trying to sample the blood from the index finger of the patient's left hand and measure blood components (for example, the blood sugar level). In blood test apparatus 40, attaching part 41a is provided on one side of housing 41. Blood sampling cartridge 42 is inserted and fixed at attaching part 41a, and blood sensor 20 is attached to one end of blood sampling cartridge 42. Further, display section 75 is provided on the other side of housing 41. As a mechanism for driving a plunger, for example, the method disclosed in Japanese Patent Application Laid-Open No. 2006-314718 can be adopted. By this means, it is possible to realize a mechanism for preventing sticking twice and a mechanism for adjusting the depth of puncturing. Further, blood test apparatus 40 may have a mechanism for adjusting the depth of puncturing, and, as an example of this mechanism, FIG. 34 shows puncturing depth adjusting control 84.

The blood test apparatus of the present invention can be used to measure glucose, and also is suitable for measuring blood components such as the lactate level and cholesterol.

INDUSTRIAL APPLICABILITY

In the blood test apparatus of the present invention, a blood sampling cartridge including a puncturing needle and a blood sensor can be attached and removed in a simple manner, and is applicable to medical equipment, and the like.

The present application is based on Japanese Patent Application No. 2006-022039, filed on Jan. 31, 2006, the entire content of which is expressly incorporated by reference herein.

The invention claimed is:

1. A blood test apparatus comprising:
a housing that comprises an opening part;
a blood sensor that is configured to be attached to the opening part; and
a plurality of connectors that are configured to connect to the blood sensor, wherein
the blood sensor comprises a supply channel in which blood is supplied; a detector is provided in the supply channel; an electrode system including a plurality of electrodes, the electrode system being provided in an area including the detector; a plurality of connection terminals that are electrically connected with each electrode of the electrode system; and a reference terminal that serves as a reference for identifying each of the plurality of connection terminals,
the plurality of connectors are configured to connect to the plurality of connection terminals and the reference terminal of the blood sensor attached at a predetermined position in the blood test apparatus, respectively,
the blood test apparatus is configured to measure electric resistance values between every two of terminals selected from the reference terminal and the plurality of connection terminals to identify the reference terminal.

2. The blood test apparatus according to claim 1, further comprising a puncturing section that is provided in the housing and punctures skin through the opening part.

3. The blood test apparatus according to claim 1, further comprising:
a plunger that moves back and forth inside the housing;
a lancet, one end of which is held by the plunger; and
a puncturing needle provided at the other end of the lancet.

4. The blood test apparatus according to claim 3, wherein the lancet, the puncturing needle and the blood sensor are integrated in a holder.

5. A blood test apparatus comprising:
a housing that comprises an opening part;
a blood sensor that is attached to the opening part and that includes a plurality of connection terminals and a reference terminal; and
a plurality of connectors that are configured to connect to the plurality of connection terminals and the reference terminal of the blood sensor attached at a predetermined position in the blood test apparatus;
the blood sensor comprises a base plate that is round or a polygon; a blood storage that is provided in the base plate, the base plate having an opening; a supply channel, one end of the supply channel communicates with the blood storage, and into which blood in the storing part flows by capillary action; a detector that is provided in the supply channel; and an air hole that communicates with the supply channel, and
the blood test apparatus further comprises a negative pressure generator that is configured to supply a negative pressure to the blood storage through the air hole,
the blood test apparatus to measure electrical resistance values between every two of terminals selected from the reference terminal and the plurality of connection terminals to identify the reference terminal.

6. The blood test apparatus according to claim 5, wherein the negative pressure section is configured to supply the negative pressure near a part punctured by a puncturing section.

7. The blood test apparatus according to claim 1, wherein:
an attaching part of the blood test apparatus comprises a guide for attaching the blood sensor to a predetermined position; and
the guide is configured to adjust a rotation angle with respect to an axis of the attached blood sensor to a predetermined angle.

8. The blood test apparatus according to claim 1, wherein:
an attaching part of the blood test apparatus comprises a guide for attaching the blood sensor to a predetermined position; and
the guide is configured to adjust a rotation angle with respect to an axis of the attached blood sensor to angles other than a predetermined angle.

9. The blood test apparatus according to claim 1, wherein electrical characteristic data for the reference terminal and each of the plurality of connection terminals of the blood sensor is reflected in internal arithmetic processing, correction, measurement order or determination.

10. A blood test apparatus comprising:
a housing that comprises an opening part;
a blood sensor that is configured to be attached to the opening part;
a plurality of connectors that are configured to connect to the blood sensor,
a plunger that moves back and forth inside the housing;
a lancet, one end of the lancet being held by the plunger; and
a puncturing needle provided at the other end of the lancet wherein
the blood sensor comprises a supply channel in which blood is supplied, a detector that is provided in the supply channel, an electrode system including a plurality of electrodes, the electrode system being provided in an area including the detector, a plurality of connection terminals that are electrically connected with each electrode of the electrode system, and a reference terminal that serves as a reference for identifying each of the plurality of connection terminals,
the plurality of connectors are configured to connect to the plurality of connection terminals and the reference terminal of the blood sensor attached at a predetermined position in the blood test apparatus, respectively,
the blood test apparatus is configured to measure electric resistance values between every two of terminals selected from the reference terminal and the plurality of connection terminals to identify the reference terminal.

11. The blood test apparatus according to claim 10, wherein the lancet, the puncturing needle and the blood sensor are integrated in a holder.

12. A blood test apparatus comprising:
a housing that comprises an opening part;
a blood sensor that is configured to be attached to the opening part; and
a plurality of connectors that are configured to connect to the blood sensor, wherein
an attaching part of the blood test apparatus comprises a guide for attaching the blood sensor to a predetermined position;
the guide is configured to control a rotation angle with respect to an axis of the attached blood sensor to a predetermined angle;
the blood sensor comprises a supply channel in which blood is supplied, a detector that is provided in the supply channel, an electrode system including a plurality of electrodes, the electrode system being provided in an area including the detector, a plurality of connection terminals that are electrically connected with each electrode of the electrode system, and a reference terminal that serves as a reference for identifying each of the plurality of connection terminals, the plurality of connectors are configured to connect to the plurality of connection terminals and the reference terminal of the blood sensor attached at a predetermined position in the blood test apparatus, respectively, the blood test apparatus is configured to measure electric resistance values between every two of terminals selected from the reference terminal and the plurality of connection terminals to identify the reference terminal.

13. A blood test apparatus comprising:

a housing that comprises an opening part;

a blood sensor that is configured to be attached to the opening part; and a plurality of connectors that are configured to connect to the blood sensor, wherein an attaching part of the blood test apparatus comprises a guide for attaching the blood sensor to a predetermined position;

the guide is configured to control a rotation angle with respect to an axis of the attached blood sensor to angles other than a predetermined angle;

the blood sensor comprises a supply channel in which blood is supplied, a detector that is provided in the supply channel; an electrode system including a plurality of electrodes, the electrode system being provided in an area including the detector; a plurality of connection terminals that are electrically connected with each electrode of the electrode system; and a reference terminal that serves as a reference for identifying each of the plurality of connection terminals, the plurality of connectors are configured to connect to the plurality of connection terminals and the reference terminal of the blood sensor attached at a predetermined position in the blood test apparatus, respectively, the blood test apparatus is configured to measure electric resistance values between every two of terminals selected from the reference terminal and the plurality of connection terminals to identify the reference terminal.

* * * * *